United States Patent
McNeff et al.

(10) Patent No.: US 10,696,923 B2
(45) Date of Patent: *Jun. 30, 2020

(54) METHODS AND APPARATUS FOR PRODUCING ALKYL ESTERS FROM LIPID FEED STOCKS, ALCOHOL FEEDSTOCKS, AND ACIDS

(71) Applicant: SarTec Corporation, Anoka, MN (US)

(72) Inventors: Charles Vincent McNeff, Andover, MN (US); Clayton V. McNeff, Andover, MN (US); Larry C. McNeff, Anoka, MN (US); Bingwen Yan, Shoreview, MN (US)

(73) Assignee: SarTec Corporation, Anoka, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/270,194

(22) Filed: Feb. 7, 2019

(65) Prior Publication Data

US 2019/0241835 A1    Aug. 8, 2019

Related U.S. Application Data

(60) Provisional application No. 62/627,511, filed on Feb. 7, 2018.

(51) Int. Cl.
    *C11C 3/00* (2006.01)
    *C11C 3/04* (2006.01)
    (Continued)

(52) U.S. Cl.
    CPC ........... *C11C 3/003* (2013.01); *B01J 21/04* (2013.01); *B01J 21/063* (2013.01); *B01J 21/066* (2013.01);
    (Continued)

(58) Field of Classification Search
    CPC .. C11C 3/003; C11C 1/002; C11C 3/04; B01J 21/04; B01J 21/063; B01J 21/066; C07C 67/02; C07C 67/03; C07C 67/08; C07C 51/15
    USPC ....................................................... 554/169
    See application file for complete search history.

(56) References Cited

U.S. PATENT DOCUMENTS

| 1,873,537 A | 8/1932 | Brown et al. |
| 2,014,408 A | 9/1935 | Woodhouse |

(Continued)

FOREIGN PATENT DOCUMENTS

| AU | 2011200090 | 2/2011 |
| BR | 8202429 | 11/1983 |

(Continued)

OTHER PUBLICATIONS

Adebanjo, Adenike O. et al., "Production of Diesel-Like Fuel and Other Value-Added Chemicals from Pyrolysis of Animal Fat," Energy & Fuels, vol. 19, 2005, pp. 1735-1741.
(Continued)

*Primary Examiner* — Deborah D Carr
(74) *Attorney, Agent, or Firm* — Pauly, DeVries Smith & Deffner LLC

(57) ABSTRACT

Embodiments herein relate to the production of alkyl esters from lipid feed stocks. In an embodiment, a process for producing alkyl esters is included. The process can include mixing a lipid feed stock with an alcohol, water, and at least one of carbon dioxide, carbon monoxide, and/or one or more acids to form a reaction mixture, and contacting the reaction mixture with a catalyst under supercritical conditions for the alcohol, the catalyst comprising a metal oxide. Other embodiments are also included herein.

19 Claims, 3 Drawing Sheets

(51) Int. Cl.
  *B01J 21/06* (2006.01)
  *B01J 21/04* (2006.01)
  *C07C 67/08* (2006.01)
  *C07C 67/02* (2006.01)
  *C11C 1/00* (2006.01)
  *C11B 13/00* (2006.01)
  *C07C 67/03* (2006.01)
  *C07C 51/15* (2006.01)

(52) U.S. Cl.
  CPC .............. *C07C 67/02* (2013.01); *C07C 67/03* (2013.01); *C07C 67/08* (2013.01); *C11B 13/00* (2013.01); *C11C 1/002* (2013.01); *C11C 3/04* (2013.01); *C07C 51/15* (2013.01)

(56) References Cited

U.S. PATENT DOCUMENTS

| | | |
|---|---|---|
| 2,154,835 A | 4/1939 | Eisenlohr |
| 2,383,632 A | 8/1945 | Trent |
| 2,679,471 A | 5/1954 | Ayers et al. |
| 2,851,468 A | 9/1958 | Snyder |
| 3,383,396 A | 5/1968 | Cahn et al. |
| 4,098,809 A | 7/1978 | Pagani |
| 4,138,336 A | 2/1979 | Mendel et al. |
| 4,216,337 A | 8/1980 | Baba et al. |
| 4,225,630 A | 9/1980 | Pitchon |
| 4,242,455 A | 12/1980 | Muller et al. |
| 4,425,433 A | 1/1984 | Neves |
| 4,487,933 A | 12/1984 | Mixan et al. |
| 4,582,589 A | 4/1986 | Ushizawa et al. |
| 4,716,218 A | 12/1987 | Chen et al. |
| 4,808,526 A | 2/1989 | Lawford |
| 4,861,739 A | 8/1989 | Pellet et al. |
| 4,885,405 A | 12/1989 | Dornhagen et al. |
| 4,891,459 A | 1/1990 | Knight et al. |
| 4,950,812 A | 1/1990 | Jacobs et al. |
| 4,911,941 A | 3/1990 | Katz et al. |
| 5,108,597 A | 4/1992 | Funkenbusch et al. |
| 5,108,897 A | 4/1992 | Steinetz et al. |
| 5,179,219 A | 1/1993 | Priegnitz |
| 5,182,016 A | 1/1993 | Funkenbusch et al. |
| 5,231,017 A | 7/1993 | Lantero et al. |
| 5,252,762 A | 10/1993 | Denton et al. |
| 5,254,262 A | 10/1993 | Funkenbusch et al. |
| 5,271,833 A | 12/1993 | Funkenbusch et al. |
| 5,298,650 A | 3/1994 | Waller et al. |
| 5,308,364 A | 5/1994 | Gutierrez et al. |
| 5,308,365 A | 5/1994 | Kesling et al. |
| 5,321,197 A | 6/1994 | Angstadt et al. |
| 5,346,619 A | 9/1994 | Funkenbusch et al. |
| 5,350,879 A | 9/1994 | Engel et al. |
| 5,389,240 A | 2/1995 | Gillespie et al. |
| 5,508,457 A | 4/1996 | Bayense et al. |
| 5,527,970 A | 6/1996 | Hwan et al. |
| 5,532,392 A | 7/1996 | Gheorghiu |
| 5,540,834 A | 7/1996 | Carr et al. |
| 5,651,953 A | 7/1997 | Yokoyama et al. |
| 5,859,270 A | 1/1999 | Kolstad et al. |
| 5,972,118 A | 1/1999 | Hester et al. |
| 5,908,946 A | 6/1999 | Stern et al. |
| 5,985,137 A | 11/1999 | Ohsol et al. |
| 6,090,959 A | 7/2000 | Hirano et al. |
| 6,153,773 A | 11/2000 | Kolstad et al. |
| 6,211,390 B1 | 4/2001 | Peter et al. |
| 6,376,701 B1 | 4/2002 | Chavan et al. |
| 6,392,062 B1 | 5/2002 | Haas |
| 6,407,269 B2 | 6/2002 | Kaita et al. |
| 6,433,146 B1 | 8/2002 | Cheryan |
| 6,441,202 B1 | 8/2002 | Lightner |
| 6,489,496 B2 | 12/2002 | Barnhorst et al. |
| 6,538,146 B2 | 3/2003 | Turck |
| 6,666,074 B2 | 12/2003 | Gerner et al. |
| 6,712,867 B1 | 3/2004 | Boocock |
| 6,713,051 B2 | 3/2004 | Mayes et al. |
| 6,719,815 B2 | 4/2004 | Nanninga et al. |
| 6,768,015 B1 | 7/2004 | Luxem et al. |
| 6,878,837 B2 | 4/2005 | Bournay et al. |
| 6,887,283 B1 | 5/2005 | Ginosar et al. |
| 6,960,672 B2 | 11/2005 | Nakayama et al. |
| 6,963,004 B2 | 11/2005 | Ahtchi-Ali et al. |
| 6,965,044 B1 | 11/2005 | Hammond et al. |
| 6,979,426 B2 | 12/2005 | Teall et al. |
| 6,982,340 B2 | 1/2006 | Mumura et al. |
| 7,045,100 B2 | 5/2006 | Ergun et al. |
| 7,097,770 B2 | 8/2006 | Lysenko |
| 7,101,464 B1 | 9/2006 | Pringle |
| 7,112,688 B1 | 9/2006 | Tysinger et al. |
| 7,126,032 B1 | 11/2006 | Aiken |
| 7,135,308 B1 | 11/2006 | Bush |
| 7,138,536 B2 | 11/2006 | Bournay et al. |
| 7,145,026 B2 | 12/2006 | Fleisher |
| 7,151,187 B2 | 12/2006 | Delfort et al. |
| 7,179,379 B2 | 2/2007 | Appel et al. |
| 7,211,681 B2 | 5/2007 | Furuta |
| 7,288,685 B2 | 10/2007 | Marker |
| 7,301,060 B2 | 11/2007 | Appel et al. |
| 7,309,592 B2 | 12/2007 | Offerman et al. |
| 7,312,355 B2 | 12/2007 | Canos et al. |
| 7,321,052 B2 | 1/2008 | Miller et al. |
| 7,371,308 B1 | 5/2008 | Hackl et al. |
| RE40,419 E | 7/2008 | Norbeck et al. |
| 7,438,785 B2 | 10/2008 | Meier et al. |
| 7,452,841 B2 | 11/2008 | Ignatchenko et al. |
| 7,476,296 B2 | 1/2009 | Appel et al. |
| 7,498,454 B2 | 3/2009 | Redlingshoefer |
| 7,501,379 B2 | 3/2009 | Ignatchenko et al. |
| 7,507,846 B2 | 3/2009 | Pelly |
| 7,514,575 B2 | 4/2009 | Ginosar et al. |
| 7,514,657 B2 | 4/2009 | Moreira et al. |
| 7,563,915 B2 | 7/2009 | Matson |
| 7,582,784 B2 | 9/2009 | Banavali et al. |
| 7,592,470 B2 | 9/2009 | Lacome et al. |
| 7,601,858 B2 | 10/2009 | Cantrell et al. |
| 7,635,398 B2 | 12/2009 | Bertram et al. |
| 7,659,432 B2 | 2/2010 | Ignatchenko et al. |
| 7,666,234 B2 | 2/2010 | Ghosh et al. |
| 7,678,163 B2 | 3/2010 | Iversen et al. |
| 7,683,232 B2 | 3/2010 | Schmidt et al. |
| 7,691,159 B2 | 4/2010 | Li |
| 7,696,376 B2 | 4/2010 | Furuta |
| 7,754,643 B2 | 7/2010 | Srinivas et al. |
| 7,771,699 B2 | 8/2010 | Adams et al. |
| 7,772,414 B1 | 8/2010 | Hybertson et al. |
| 7,777,085 B2 | 8/2010 | Berry et al. |
| 7,780,946 B2 | 8/2010 | Wormsbecher |
| 7,790,651 B2 | 9/2010 | Lin |
| 7,850,841 B2 | 12/2010 | Koivusalmi et al. |
| 7,851,643 B2 | 12/2010 | Hillion et al. |
| 7,857,872 B2 | 12/2010 | Krasutsky et al. |
| 7,880,043 B2 | 2/2011 | Chapus et al. |
| 7,883,882 B2 | 2/2011 | Franklin et al. |
| 7,897,798 B2 | 3/2011 | Mcneff |
| 7,925,273 B2 | 4/2011 | Fomukong et al. |
| 7,928,273 B2 | 4/2011 | Bradin |
| 7,935,515 B2 | 5/2011 | Franklin et al. |
| 7,943,791 B2 | 5/2011 | Mcneff |
| 7,967,973 B2 | 6/2011 | Myllyoja et al. |
| 7,998,339 B2 | 8/2011 | Myllyoja et al. |
| 8,003,833 B2 | 8/2011 | Appel et al. |
| 8,008,516 B2 | 8/2011 | Cantrell et al. |
| 8,017,796 B2 | 9/2011 | Mcneff et al. |
| 8,022,258 B2 | 9/2011 | Myllyoja et al. |
| 8,076,498 B2 | 12/2011 | Elst et al. |
| 8,361,174 B2 | 1/2013 | McNeff et al. |
| 8,445,709 B2 | 5/2013 | Mcneff et al. |
| 8,466,305 B2 | 6/2013 | Mcneff |
| 8,585,976 B2 | 11/2013 | Mcneff et al. |
| 8,686,171 B2 | 4/2014 | Mcneff et al. |
| 8,697,893 B2 | 4/2014 | Mcneff et al. |
| 9,102,877 B2 | 8/2015 | Mcneff et al. |
| 9,382,491 B2 | 7/2016 | Mcneff et al. |
| 9,388,345 B2 | 7/2016 | Mcneff et al. |
| 10,239,812 B2 | 3/2019 | Fedie et al. |

(56) References Cited

U.S. PATENT DOCUMENTS

| | | |
|---|---|---|
| 2001/0042340 A1 | 11/2001 | Tateno et al. |
| 2002/0010359 A1 | 1/2002 | Kaita et al. |
| 2002/0156305 A1 | 10/2002 | Turck |
| 2002/0173682 A1 | 11/2002 | Tullio et al. |
| 2003/0032819 A1 | 2/2003 | Lightner |
| 2003/0143156 A1 | 7/2003 | Wormsbecher |
| 2003/0199049 A1 | 10/2003 | Nguyen et al. |
| 2003/0199149 A1 | 10/2003 | Lee et al. |
| 2003/0229238 A1 | 12/2003 | Fleisher |
| 2004/0074760 A1 | 4/2004 | Portnoff et al. |
| 2004/0087809 A1 | 5/2004 | Nakayama et al. |
| 2004/0094477 A1 | 5/2004 | Lysenko et al. |
| 2004/0188340 A1 | 9/2004 | Appel et al. |
| 2004/0192980 A1 | 9/2004 | Appel et al. |
| 2004/0192981 A1 | 9/2004 | Appel et al. |
| 2005/0006290 A1 | 1/2005 | Patten |
| 2005/0064577 A1 | 3/2005 | Berzin |
| 2005/0080280 A1 | 4/2005 | Yoo |
| 2005/0112739 A1 | 5/2005 | Golubkov |
| 2005/0118409 A1 | 6/2005 | Mcneff et al. |
| 2005/0137411 A1 | 6/2005 | Ahtchi-Ali et al. |
| 2005/0204612 A1 | 9/2005 | Connemann et al. |
| 2005/0239182 A1 | 10/2005 | Berzin |
| 2005/0260553 A1 | 11/2005 | Berzin |
| 2005/0261509 A1 | 11/2005 | Delfort et al. |
| 2005/0266139 A1 | 12/2005 | Lacome et al. |
| 2005/0274065 A1 | 12/2005 | Portnoff et al. |
| 2006/0004237 A1 | 1/2006 | Appel et al. |
| 2006/0014974 A1 | 1/2006 | Bournay et al. |
| 2006/0041152 A1 | 2/2006 | Cantrell et al. |
| 2006/0041153 A1 | 2/2006 | Cantrell et al. |
| 2006/0043003 A1 | 3/2006 | Moreira et al. |
| 2006/0080891 A1 | 4/2006 | Ghosh et al. |
| 2006/0135823 A1 | 6/2006 | Jun et al. |
| 2006/0149087 A1 | 7/2006 | Furuta |
| 2006/0224005 A1 | 10/2006 | Felly |
| 2006/0246141 A1 | 11/2006 | Liversidge et al. |
| 2006/0252950 A1 | 11/2006 | Ginosar et al. |
| 2006/0260186 A1 | 11/2006 | Iversen et al. |
| 2006/0288636 A1 | 12/2006 | Iijima et al. |
| 2007/0010682 A1 | 1/2007 | Myllyoja et al. |
| 2007/0027338 A1 | 2/2007 | Furuta |
| 2007/0037994 A1 | 2/2007 | Canos et al. |
| 2007/0066838 A1 | 3/2007 | Hillion et al. |
| 2007/0089356 A1 | 4/2007 | Krasutsky et al. |
| 2007/0093380 A1 | 4/2007 | Srinivas et al. |
| 2007/0098625 A1 | 5/2007 | Adams et al. |
| 2007/0137097 A1 | 6/2007 | Ikura |
| 2007/0196892 A1 | 8/2007 | Winsness et al. |
| 2007/0225383 A1 | 9/2007 | Cortright et al. |
| 2007/0238905 A1 | 10/2007 | Arredondo et al. |
| 2007/0282118 A1 | 12/2007 | Gupta et al. |
| 2007/0283619 A1 | 12/2007 | Hillion et al. |
| 2008/0051592 A1 | 2/2008 | Mcneff et al. |
| 2008/0161615 A1 | 7/2008 | Chapus |
| 2008/0188676 A1 | 8/2008 | Anderson et al. |
| 2008/0194811 A1 | 8/2008 | Mcneff |
| 2008/0197052 A1 | 8/2008 | Mcneff et al. |
| 2008/0275144 A1 | 11/2008 | Van Hardeveld et al. |
| 2008/0318763 A1 | 12/2008 | Anderson |
| 2008/0319236 A1 | 12/2008 | Mcneff et al. |
| 2009/0014354 A1 | 1/2009 | Knuuttila et al. |
| 2009/0029445 A1 | 1/2009 | Eckelberry et al. |
| 2009/0069586 A1 | 3/2009 | Oku et al. |
| 2009/0126262 A1 | 5/2009 | Asthana et al. |
| 2009/0227823 A1 | 9/2009 | Huber et al. |
| 2009/0255171 A1 | 10/2009 | Dumesic et al. |
| 2009/0281056 A1 | 11/2009 | Mori et al. |
| 2009/0297495 A1 | 12/2009 | Kerovuo et al. |
| 2010/0010246 A1 | 1/2010 | Yan et al. |
| 2010/0048930 A1 | 2/2010 | Elst et al. |
| 2010/0050502 A1 | 3/2010 | Wu et al. |
| 2010/0081181 A1 | 4/2010 | Berry et al. |
| 2010/0081835 A1 | 4/2010 | Wu et al. |
| 2010/0087670 A1 | 4/2010 | Wang et al. |
| 2010/0113849 A1 | 5/2010 | Bartek et al. |
| 2010/0147771 A1 | 6/2010 | Mcneff et al. |
| 2010/0151535 A1 | 6/2010 | Franklin et al. |
| 2010/0151539 A1 | 6/2010 | Franklin et al. |
| 2010/0170143 A1 | 7/2010 | Mcneff et al. |
| 2010/0170147 A1 | 7/2010 | Mcneff et al. |
| 2010/0191004 A1 | 7/2010 | Mcneff et al. |
| 2010/0287823 A1 | 11/2010 | Misra et al. |
| 2010/0305346 A1 | 12/2010 | Hara et al. |
| 2010/0324310 A1 | 12/2010 | Dumesic et al. |
| 2011/0009501 A1 | 1/2011 | Ernst |
| 2011/0035993 A1 | 2/2011 | Loescher |
| 2011/0060153 A1 | 3/2011 | Mcneff et al. |
| 2011/0105814 A1 | 5/2011 | Koivusalmi et al. |
| 2011/0172450 A1 | 7/2011 | Mcneff et al. |
| 2011/0184201 A1 | 7/2011 | Mcneff |
| 2011/0213040 A1 | 9/2011 | Hassan et al. |
| 2011/0287991 A1 | 11/2011 | Dubois |
| 2011/0306808 A1 | 12/2011 | Appel et al. |
| 2011/0319849 A1 | 12/2011 | Collias et al. |
| 2012/0055077 A1 | 3/2012 | Savage et al. |
| 2013/0345457 A1 | 12/2013 | McNeff |
| 2014/0046104 A1 | 2/2014 | Mcneff et al. |
| 2014/0115955 A1 | 5/2014 | Mcneff et al. |
| 2017/0029711 A1 | 2/2017 | Mcneff et al. |
| 2018/0312457 A1 | 11/2018 | Fedie et al. |

FOREIGN PATENT DOCUMENTS

| | | |
|---|---|---|
| BR | 06001602 | 10/2007 |
| CA | 2601472 | 9/2006 |
| CA | 2607931 | 11/2006 |
| CA | 2660049 | 9/2015 |
| CN | 1680514 | 10/2005 |
| CN | 1718679 | 1/2006 |
| CN | 1858160 | 11/2006 |
| CN | 1887417 | 1/2007 |
| CN | 1928016 | 3/2007 |
| CN | 101870989 | 10/2010 |
| DE | 19620378 | 2/1999 |
| DE | 102004056786 | 7/2005 |
| DE | 102005038137 | 2/2007 |
| EP | 0169953 | 2/1986 |
| EP | 0198243 | 10/1986 |
| EP | 0506428 A1 | 9/1992 |
| EP | 0535290 | 4/1993 |
| EP | 1396483 A1 | 3/2004 |
| EP | 1505048 | 2/2005 |
| EP | 1580255 | 9/2005 |
| EP | 1607467 | 12/2005 |
| EP | 1642560 | 4/2006 |
| EP | 1681281 | 7/2006 |
| EP | 1869173 | 12/2007 |
| EP | 0507217 A1 | 10/2010 |
| EP | 2290035 | 3/2011 |
| EP | 2290045 | 3/2011 |
| FR | 2188612 A5 | 1/1974 |
| FR | 2679471 | 1/1993 |
| FR | 2890656 | 3/2007 |
| FR | 2938536 | 5/2010 |
| FR | 2947564 | 1/2011 |
| GB | 2132222 | 7/1984 |
| JP | 02289692 | 11/1990 |
| JP | 6313188 | 11/1994 |
| JP | 11228494 | 8/1999 |
| JP | 2000355692 | 12/2000 |
| JP | 2005126346 | 5/2005 |
| JP | 2005177722 | 7/2005 |
| JP | 2006129735 | 5/2006 |
| JP | 2007153943 | 6/2007 |
| JP | 2007153944 | 6/2007 |
| JP | 2007190450 | 8/2007 |
| JP | 2008111085 | 5/2008 |
| WO | 9108677 | 6/1991 |
| WO | 1996027632 | 9/1996 |
| WO | 9707187 | 2/1997 |
| WO | 9950213 | 10/1999 |
| WO | 2000005327 A1 | 2/2000 |
| WO | 02102337 | 12/2002 |

(56) References Cited

FOREIGN PATENT DOCUMENTS

| | | |
|---|---|---|
| WO | 03/062358 | 7/2003 |
| WO | 03/087279 | 10/2003 |
| WO | 03094598 | 11/2003 |
| WO | 2004/085585 | 10/2004 |
| WO | 2004096962 | 11/2004 |
| WO | 2004108873 | 12/2004 |
| WO | 2005/000782 | 1/2005 |
| WO | 2005/021697 A1 | 3/2005 |
| WO | 2005/035479 | 4/2005 |
| WO | 2005/093015 | 10/2005 |
| WO | 2005/123890 | 12/2005 |
| WO | 2006041253 | 4/2006 |
| WO | 2006/070661 | 7/2006 |
| WO | 2006/081644 | 8/2006 |
| WO | 2006/088254 | 8/2006 |
| WO | 2006/093896 | 9/2006 |
| WO | 2006/094986 | 9/2006 |
| WO | 2006096834 | 9/2006 |
| WO | 2006121584 | 11/2006 |
| WO | 2007/011343 | 1/2007 |
| WO | 2007/012190 | 2/2007 |
| WO | 2007/025360 | 3/2007 |
| WO | 2007/029851 | 3/2007 |
| WO | 2007/038605 | 4/2007 |
| WO | 2007/043062 | 4/2007 |
| WO | 2007068097 | 6/2007 |
| WO | 2007072972 | 6/2007 |
| WO | 2007077950 | 7/2007 |
| WO | 2007111604 | 10/2007 |
| WO | 2007140395 | 12/2007 |
| WO | 2007141293 | 12/2007 |
| WO | 2007142983 | 12/2007 |
| WO | 2007146636 A1 | 12/2007 |
| WO | 2008012275 | 1/2008 |
| WO | 2008019325 | 2/2008 |
| WO | 2008/034109 | 3/2008 |
| WO | 2008029132 | 3/2008 |
| WO | 2008041038 | 4/2008 |
| WO | 2008101007 | 8/2008 |
| WO | 2008101032 | 8/2008 |
| WO | 2008152199 | 12/2008 |
| WO | 2009002880 A1 | 12/2008 |
| WO | 2009003039 | 12/2008 |
| WO | 2009007234 | 1/2009 |
| WO | 2009115322 | 9/2009 |
| WO | 2009143159 | 11/2009 |
| WO | 2010005391 | 1/2010 |
| WO | 2010036333 | 4/2010 |
| WO | 2010075437 A3 | 7/2010 |
| WO | 2010132628 | 11/2010 |
| WO | 2010141794 | 12/2010 |
| WO | 2010144597 | 12/2010 |
| WO | 2010147955 | 12/2010 |
| WO | 2010148057 | 12/2010 |
| WO | 2011004111 | 1/2011 |
| WO | 2011012438 | 2/2011 |
| WO | 2011012439 | 2/2011 |
| WO | 2011012440 | 2/2011 |
| WO | 2011130573 | 10/2011 |
| WO | 2011150410 | 12/2011 |
| WO | 2011150411 | 12/2011 |
| WO | 2014008355 | 1/2014 |
| WO | 2016149692 | 9/2016 |

OTHER PUBLICATIONS

Aimaretti, N. et al., "Batch Study of Glycerol Decomposition in One-Stage Supercritical Production of Biodiesel," Energy & Fuels 2009, vol. 23, pp. 1076-1080.

Akhtar, Javaid et al., "A Review on Process Conditions for Optimum Bio-Oil Yield in Hydrothermal Liquefaction of Biomass," Renewable and Sustainable energy Reviews 15 (2011), pp. 1615-1624.

Albrecht, Ko et al., "A Brief Literature Overview of Various Routes to Biorenewable Fuels from Lipids for the National Alliance for Advanced Biofuels and Bio-products (NAABB) Consortium," U.S. Department of Energy, PNNL-20279, 2011, pp. 1-16.

Alonso, David M. et al., "Catalytic Conversion of Biomass to Biofuels," Green Chem., vol. 12, 2010, pp. 1493-1513.

Alonso, David M. et al., "Production of Liquid Hydrocarbon Transportation Fuels by Oligomerization of Biomass-Derived C9 Alkenes," Green Chem., vol. 12, 2010, pp. 992-999.

An, Lu et al., "The Influence of Ni Loading Coke Formation in Steam Reforming of Acetic Acid," Renewable Energy, vol. 36, 2011, pp. 930-935.

Annen, et al., "Development of Porous Zirconia Spheres by Polymerization-Induced Colloid Aggregation-Effect of Polymerization Rate," Journal of Mater. Sci., 29(23):6123-6130 (1994).

Anon, "Beatrice Biodiesel Selects Axens Exterfip-H Technology," Biodiesel Magazine Jun. 2006, Unknown.

Barteau, Mark A. "Organic Reactions at Well-Defined Oxide Surfaces," Chem. Rev., vol. 96, 1996, pp. 1413-1430.

Bcc Research, "Global Market for Catalyst Regeneration," MarketResearch.com http://www.marketresearch.com/product/display.asp?productid=1354464 2006, 1-20.

Beckman, Eric J. "Supercritical and near-critical CO2 in green chemical synthesis and processing," J. of Supercritical Fluids 28 (2004) 121-191 (71 pages).

Bertoldi, Cristiane et al., "Continuous Production of Biodiesel from Soybean Oil in Supercritical Ethanol and Carbon Dioxide as Cosolvent," Energy Fuels 2009, 23, 5165-5172 (8 pages).

Bicker, et al., Green Chemistry 2003, 5. 2005, 280-284.

Billaud, F. et al., "Catalytic Cracking of Octanoic Acid," Journal of Analytical and Applied Pyrolysis, vol. 58-59, 2001, pp. 605-616.

Billaud, Francis et al., "Pyrolysis of Secondary Raw Material from Used Frying Oils," Récents Progrès en Génie des Procédés, Numéro 94—2007 ISBN 2-910239-68-3, Ed. SFGP, Paris, France (8 pages).

Blackwell, J. A. et al., "A Chromatographic Study of the Lewis Acid-Base Chemistry of Zirconia Surfaces," J. Liquid Chromatog. 1991, 14: 2875-2889.

Blackwell, J. A. et al., "Study of the Fluoride Adsorption Characterisitics of Porous Microparticulate Zirconium Oxide," J. Chromatog. 1991, 549: 43-57.

Bournay, L. et al., "New Heterogeneous Process for Biodiesel Production: A Way to Improve the Quality and the Value of the Crude Glycerin Produced by Biodiesel Plants," Catalysis Today 2005, 106: 190-192.

Brown, Adrian S. et al., "Sulfated Metal Oxide Catalysts: Superactivity through Superacidity?," Green Chemistry Feb. 1999, 17-20.

Bryan, Tom "Adsorbing It All," Biodiesel Magazine Mar. 2005, 40-43.

Busca, Guido "Bases and Basic Materials in Industrial and Environmental Chemistry: A Review of Commerical Processes," Ind. Eng. Chem. Res., vol. 48, 2009, pp. 6486-6511.

Cao, W. et al., "Preparation of Biodiesel from Soybean Oil Using Supercritical Methanol and Co-Solvent," Fuel 2005, 84: 347-351.

Catallo, W. J. et al., "Transformation of Glucose to Volatile and Semi-Volatile Products in Hydrothermal (HT) Systems," Biomass and Bioenergy, vol. 34, 2010, pp. 1-13.

Chen, Ching-Hung et al., "Biodiesel Production from Supercritial Carbon Dioxide Extracted Jatropha Oil Using Subcritical Hydrolysis and Supercritical Methylation," J. of Supercritical Fluids, vol. 52, 2010, pp. 228-234.

Chen, Ching-Hung et al., "Subcritical Hydrolysis and Supercritical Methylation of Supercritical Carbon Dioxide Extraction of Jatropha Oil," Separation and Purification Technology, vol. 74, 2010, pp. 7-13.

Cheng, F W. "China Produces Fuels from Vegetable Oils," Chem. Metall. Eng. Jan. 1945, 99.

Chheda, et al., Catalysis Today 2007 123. 2007, 59-70.

Choudhary, T. V. et al., "Renewable Fuels via Catalytic Hydrodeoxygenation," Applied Catalysis A: General, vol. 397, 2011 pp. 1-12.

(56) References Cited

OTHER PUBLICATIONS

Collins, K. "Statement of Keith Collins, Chief Economist, U.S. Department of Agriculture before the U.S. Senate Committee on Appropriations, Subcommittee on Agriculture, Rural Development, and Related Agencies: Economic Issues Related to Biofuels.," Unknown www.usda.gov/documents/Farmbill07energy.doc. Aug. 26, 2006, 1-8 (web).
Cottier, et al., Heterocyclic Chemistry 1991, 2. 1991, 233-248.
Czernik, Stefan et al., "Hydrogen by Catalytic Steam Reforming of Liquid Byproducts from biomass Thermoconversion Processes," Ind. Eng. Chem. Res. vol. 41, 2002, pp. 4209-4215.
Dagle, Robert A. et al., "Methanol Steam Reforming for Hydrogen Production," Chem. Rev., vol. 107, 2007, pp. 3992-4021.
Dandik, Levent et al., "Catalytic Conversion of Used Oil to Hydrocarbon Fuels in a Fractionating Pyrolysis Reactor," Energy and Fuels, vol. 12, 1998, pp. 1148-1152.
Danuthai, Tanate et al., "Conversion of Methylesters to Hydrocarbons over an H-ZSM5 Zeolite Catalyst," Applied Catalyst A: General. vol. 361, 2009, pp. 99-105.
De La Casa, R.M. et al., "Modification of the Activities of Two Different lipases from Candida Rugosa with Dextrans," Enzyme and Microbial Technology, vol. 30, 2002, pp. 30-40.
De Lasa, Hugo et al., "Catalytic Steam Gasificationof Biomass: Catalysts, Thermodynamics and Kinetics," Chemical Reviews, vol. 111, 2011, pp. 5404-5433.
De Paula, Ariela V. et al., "Screening of Food Grade Lipases to be Used in Esterification and Interesterification Reactions of Industrial Interest," Appl Biochem Biotechnol, vol. 160, pp. 1146-1156.
Dean, Morgan et al., "Nanocrystalline Metal Oxide-Based Catalysts for Biodiesel Production from Soybean Oil," #96—Student Poster Session: Catalysis & Reaction Engineering (04016) http://aiche.confex.com/aiche/2006/techprogram/P78366.HTM Nov. 13, 2006, 1 (web).
Demirbas, Ayhan "Biodiesel fuels from vegetable oils via catalytic and non-catalytic supercritical alcohol transesterifications and other methods: a survey," Energy Conversion & Management 2003, issue 44 pp. 2093-2109.
Deng, Li et al., "Upgraded Acidic Components of Bio-Oil through Catalytic Ketonic Condensation," Energy & Fuels, vol. 23, 2009, pp. 564-568.
Di Serio, et al., "Synthesis of Biodiesel via Homogeneous Lewis Acid Catalyst," J. Molec. Catal. A Chem. 2005, 239: 111-115.
Di Serio, M. et al., "Transesterification of Soybean Oil to Biodiesel by Using Heterogeneous Basic Catalysts," Ind. Eng. Chem. Res. 2006, 45: 3009-3014.
Dias, et al., Journal of Catalysis, 2005, 229 2005, 414-423.
Dierker, Markus et al., "Surfactants from Oleic, Erucic, and Petroselinic Acid: Synthesis and Properties," Eur. J. Lipid Sci. Technol., vol. 112, 2010, pp. 122-136.
Dme Project At Air Products, "Liquid Phase Dimethyl Ether Demonstration in the LaPorte Alternative Fuels Development Unit," Air Products and Chemicals, Inc., Allentown, Pennsylvania (Jan. 2001).
Dorsa, Renato et al., "Basics of Alkali Refining of Vegetable Oils," GEA Westfalia Separator Food Tec GmbH Unknown, 1-28.
Dry, Mark E. "The Fischer-Tropsch process—Commercial Aspects," Catalysis today 6 (3), 1990, pp. 183-206.
Dry, Mark E. et al., "High Quality Diesel via the Fischer-Tropsch Process—A Review," J. Chem Technol Biotechnol., vol. 77, 2001, pp. 43-50.
Dunlap, C. J. et al., "Zirconia Stationary Phases for Extreme Separations," Anal. Chem. 2001, 73: 598A-607A.
Elliott, Brian "Low-cost Biodiesel Production Process Using Waste Oils and Fats," U.S. EPA SBIR Phase I Kick-Off Meeting www.iastate.edu/Inside/2003/0613/biorenewable.jpg Apr. 5, 2007, 1.
Fabbri, D. et al., "Dimethyl carbonate as a novel methylating reagent for fatty acidsin analytical pyrolysis," Journal of Chromatography, Elsevier Science Publishers B.V, NL LNKDD01:I0.I016/J.CHROMA. 2004.12.077 Feb. 18, 2005.
File History for U.S. Appl. No. 12/987,751 downloaded May 31, 2018 (429 pages).
File History for U.S. Appl. No. 11/833,839 downloaded May 31, 2018 (360 pages).
File History for U.S. Appl. No. 12/030,801 downloaded May 31, 2018 (325 pages).
File History for U.S. Appl. No. 12/146,175 downloaded May 31, 2018 (259 pages).
File History for U.S. Appl. No. 13/080,507 downloaded May 31, 2018 (264 pages).
File History for U.S. Appl. No. 13/909,885 downloaded May 31, 2018 (147 pages).
File History for U.S. Appl. No. 12/540,568 downloaded May 31, 2018 (257 pages).
File History for U.S. Appl. No. 12/797,393 downloaded (237 pages).
File History for U.S. Appl. No. 12/030,649 downloaded May 31, 2018 (252 pages).
File History for U.S. Appl. No. 12/238,750 downloaded May 31, 2018 (202 pages).
File History for U.S. Appl. No. 12/575,198 downloaded May 31, 2018 (296 pages).
File History for U.S. Appl. No. 12/645,119 downloaded May 31, 2018 (316 pages).
File History for U.S. Appl. No. 12/617,125 downloaded May 31, 2018 (375 pages).
File History for U.S. Appl. No. 14/146,601 downloaded Jun. 1, 2018 (359 pages).
File History for U.S. Appl. No. 13/934,713 downloaded Jun. 1, 2018 (1062 pages).
File History for European Patent Application No. 07840692.3 downloaded Jun. 19, 2018 (375 pages).
File History for European Patent Application No. 08729792.5 downloaded Jun. 19, 2018 (262 pages).
File History for European Patent Application No. 08771929.0 downloaded Jun. 19, 2018 (137 pages).
File History for European Patent Application No. 10724652.2 downloaded Jun. 19, 2018 (205 pages).
File History for European Patent Application No. 08729762.8 downloaded Jun. 19, 2018 (216 pages).
File History for U.S. Appl. No. 15/189,428 downloaded Apr. 15, 2019 (1694 pages).
File History for U.S. Appl. No. 15/963,583 downloaded Apr. 15, 2019 (263 pages).
Frykman, Hans B. et al., "Screening Catalytic Lipase Activities with an Analytical Supercritical Fluid Extractor," JAOCS, vol. 75, 1998, pp. 517-520.
Fu, Jie et al., "Activated Carbons for Hydrothermal Decarboxylation of Fatty Acids," ACS Catalysis, vol. 1, 2011, pp. 227-231.
Fu, Jie et al., "Catalytic Hydrothermal Deoxygenation of Palmitic Acid," Energy Environ. Sci., vol. 3, 2010, pp. 311-317.
Fujita, Kazunori et al., "Hydrolysis of Glycerol Trioleate and Extraction of Its Fatty acid Under Co2 Supercritical Conditions," The Chemical Society of Japan, vol. 1, 1995, pp. 79-82.
Fureby, Anna M. et al., "Preparation of Diglycerides by Lipase-Catalyzed Alcoholysis of Triglycerides," Enzyme and Microbial Technology, vol. 20, 1997, pp. 198-206.
Furuta, S. et al., "Biodiesel Fuel Production with Solid Superacid Catalysis is Fixed Bed Reactor Under Atmospheric Pressure," Catalysis Communications 2004, 5: 721-723.
Gaertner, C. A. et al., "Catalytic Coupling of Carboxylic Acids by Ketonization as a Processing Step in Biomass Conversion," Journal of Catalysis, vol. 266, 2009, pp. 71-78.
Gaertner, Christian A. et al., "Catalytic Upgrading of Bio-Oils by Ketonization," ChemSusChem, vol. 2, 2009, pp. 1121-1124.
Gaertner, Christian A. et al., "Ketonization Reactions of Carboxylic Acids and Esters over Ceria-Zirconia as Biomass-Upgrading Processes," Ind. Eng. Chem. Res, vol. 49, 2010, pp. 6027-6033.
Gercel, H. F. et al., "Hydropyrolysis of Extracted Euphorbia rigida in a Well-Swept Fixed-Bed Tubular Reactor," Energy Sources 2002, 24: 423-430.
Glinski, M. et al., "Catalytic Ketonization over Oxide Catalysts X. Transformations of Various Alkyl Heptanoates," Applied Catalysis A: General, vol. 281, 2005, pp. 107-113.

(56) References Cited

OTHER PUBLICATIONS

Glinski, M. et al., "Ketones from Monocarboxylic acids: Catalytic Ketonization over Oxide Systems," Applied Catalysis A: General, vol. 128, 1995, pp. 209-217.

Goering, C. E. et al., "Fuel Properties of Eleven Vegetable Oils," Trans ASAE 1982, 25: 1472-1477.

Goodwin, J. G. "Research Activities: Biodiesel Synthesis," Chemical and Biomolecular Engineering at Clemson University http://www.ces.clemson.edu/chemeng/facultypages/goodwin/research.html 2006, 1-5.

Guerbuez, Elif I. et al., "Dual-Bed Catalyst System for C—C Coupling of Biomass-Derived Oxygenated Hydrocarbons to Fuel-Grade Compounds," Green Chemistry, vol. 12, 2010, pp. 223-227.

Guthalugu, Nagesha K. et al., "Optimization of Enzymatic Hydrolysis of Triglycerides in Soy Deodorized Distillate with Supercritical Carbon Dioxide," Biochemical Engineering Journal, vol. 29, 2006, pp. 220-226.

Haas, M. J. et al., "Engine Performance of Biodiesel Fuel Prepared from Soybean Soapstack: A High Quality Renewable Fuel Produced from a Waste Feedstock," Energy Fuels 2001, 15: 1207-1212.

Haas, M. J. et al., "Improving the Economics of Biodiesel Production Through the Use of Low Value Lipids as Feedstocks: Vegetable Oil soapstock," Fuel Process. Technol. 2005, 86: 1087-1096.

Hampson, J.W. et al., "Effect of Moisture Content on Immobilized Lipase-Catalyzed Tricylglycerol Hydrolysis Under Supecritical Carbon Dioxide Flow in a Tubular Fixed-Bed Reactor," JAOCS, vol. 76, 1999, pp. 777-781.

Hampson, J.W. et al., "Separation of Tripalmitin from Its Hydrolysis Products by Simple Isocratic Reversed-Phase High-Performance Liquid Chromatography," JAOCS, vol. 75, 1998, pp. 539-540.

Hara, Michikazu "Biomass conversion by a solid acid catalyst," Energy Environ. Sci., vol. 3, 2010, pp. 601-607.

Harvey, A. P. et al., "Process Intensification of Biodiesel Production Using a Continuous Oscillatory Flow Reactor," J. Chem. Technol. Biotechnol. 2003, 78: 338-341.

Haryanto, Agus et al., "Current Status of Hydrogen Production Techniques by Steam Reforming of Ethanol: A Review," Energy and Fuels, vol. 19, 2005, pp. 2098-2106.

He, Chen et al., "Biodiesel from Transesterification of Cotton Seed Oil by Solid Bases Catalysis," Journal of Chemical Engineering of Chinese Universities Aug. 2006, No. 4 vol. 20.

He, Chen et al., "Biodiesel Production by the transesterification of cottonseed oil by solid acid catalysts," Frontiers of Chemical Engineering in China Feb. 2006, vol. 1, No. 1, pp. 1673-7369.

Henry, R. A. et al., "A Novel Chemical Route to Stable, Regenerable Zirconia-Based Chiral Stationary Phases for HPLC," American Laboratory (News Edition) 2005, 37: 22-24.

Heyerdahl, Petter H. et al., "Hydrothermal Treatment and Microwave Assisted Pyrolysis of Biomass for Bio-fuel Production-Progress Report," Presentation at UMB and UMN 2006, pp. 1-45.

Hill, J. et al., "Environmental, Economic, and Energetic Costs and Benefits of Biodiesel and Ethanol Biofuels," PNAS 2006, 103(30): 11206-11210.

Hirata, Hirofumi et al., "Enzyme Reaction in Organic Solvent. III. Effect of Water Content and Inhibition of Alcohol for the Catalyzed Transesterification in Tributyrin 1-Octanol," Natl. Chem. Lab. Ind., vol. 38, 1989, pp. 48-52.

Hirata, Hirofumi et al., "Substrate-Solvent Dependence of Enantioselectivity in Porcine Pancreatic Lipase Catalyzed Transesterification Between Tributyrylglycerol and Secondary Alcohol in Organic Solvent," J. Oleo Sci., vol. 51, 2002, pp. 539-547.

Holliday, Russell L. et al., "Hydrolysis of Vegetable Oils in Sub- and Supercritical Water," Industrial and Engineering Chemistry Research, vol. 36, No. 3, 1997, pp. 932-935.

Idem, Raphael O. et al., "Thermal Cracking of Canola Oil: Reaction Products in the Presence and Absence of Steam," Energy & Fuels . vol. 10, 1995, pp. 1150-11662.

Ignatchenko, Alexey et al., "Interaction of Water with Titania and Zirconia Surfaces," Journal of Molecular Catalysis A: Chemical, vol. 256, 2006, pp. 57-74.

Ignatchenko, Alexey V. "Density Functional Theory Study of Carboxylic Acids Adsorption and Enolization on Monoclinic Zirconia Surfaces," J. Phys. Chem. C., vol. 116, pp. 16012-16018.

Iijima, Wataru et al., "The Non-glycerol Process of Biodiesel Fuel Treated in Supercritical Methanol (Abstract)," Paper No. 046073, 2004 ASAE Annual Meeting 2004, 1.

Iijima, Wataru et al., "Winterized" Bio-Diesel Fuel Produced from Animal Fat, Agro-Energy Laboratory, Dept. of Farm Mechanization and Engineering,National Agricultural ResearchCentre, National Agricultural Research Organization, Japan Unknown, 1-2.

Immer, Jeremy G. et al., "Catalytic Reaction Pathways in Liquid-Phase Deoxygenation of C18 Free Fatty Acids," Applied Catalysis A: General, vol. 375, 2010, pp. 134-139.

"International Preliminary Report on Patentability," For PCT Application No. PCT/US2013/049250, dated Jan. 15, 2015 (8 pages).

International Search Report and Written Opinion for International Application No. PCT/US2007/075211 dated Jul. 9, 2008 (10 pages).

International Search Report and Written Opinion for International Application No. PCT/US2008/053883 dated Jul. 9, 2008 (9 pages).

"International Search Report and Written Opinion," for International Application No. PCT/US2009069280, corresponding to U.S. Appl. No. 12/645,119, dated Sep. 13, 2010, (20 pages).

"International Search Report and Written Opinion," for PCT/US2013/049250, dated Nov. 1, 2013 (11 pages).

Irimescu, Roxana et al., "Comparison of Acyl Donors for Lipase-Catalyzed Production of 1,3-Dicapryloyl-2-eicosapentaenoylglycerol," JAOCS, vol. 78, 2001, pp. 65-70.

Isayama, Yohei et al., "Biodiesel production by supercritical process with crude bio-methanol prepared by wood gasification," Bioresource Technology, vol. 99, 2008, pp. 4775-4779.

Ishai, Paul B. et al., "Influence of Cyclosporine A on Molecular Interactions in Lyotropic Reverse Hexagonal Liquid Crystals," J. Phys. Chem. B, vol. 114, 2010, pp. 12785-12791.

Ishihara, K. et al., "Direct Ester Condensation from a 1:1 Mixture of Carboxylic Acids and Alcohols Catalyzed by Hafnium (IV) or Zirconium (IV) Salts.," Tetrahedron 2002, 58: 8179-8188.

Isono, Yasuyuki et al., "Interesterification of Triglyceride and Fatty Acid in a Mircoaqueous Reaction System Using Lipase-Surfactant Complex," Biosci. Biotech. Biochem., vol. 59 (9), 1995, 1632-1635.

Jiang, Xiaoxing et al., "Upgrading Bio-Oil Through Emulsification with Biodiesel: Thermal Stability," Energy Fuels, vol. 24, 2010, pp. 2699-2706.

Jimenez-Morales, I. et al., "Calcined zirconium sulfate supported on MCM-41 silica as acid catalyst for ethanolysis of sunflower oil," Applied Catalysis B: Environmental, vol. 103, 2011, pp. 91-98.

Kahn, A. "Research into Biodiesel Catalyst Screening and Development," Thesis, University of Queensland Brisbane 2002, 1-41.

Kamimura, Yoichiro et al., "Synthesis of 3-Pentanone from 1-Propanol Over Ce02—Fe2O3 Catalysts," Applied catalysis A: General, vol. 252, (2003), pp. 399-410.

Katsivela, E. et al., "Hydrolysis and Ester-Synthesis Activties of Crude Enzyme Preparation," Enzyme and Microbial technology, vol. 17, 1995, pp. 739-745.

Kim, K.S. et al., "Pathways for Carboxylic Acid Decomposition of TiO2," Langmuir, vol. 4, 1988, pp. 945-953.

King, Jerry W. et al., "Hydrolysis of soybean oil in a subcritical water flow reactor," Green Chemistry, vol. 1, 1999, pp. 261-264.

Kiss, Anton A. et al., "Solid Acid Catalysts for Biodiesel Production—Towards Sustainable Energy," Adv. Synth. Catal. 2006, 348: 75-81.

Kittelson, "Biofuels for Engines," Third Annual IREE Research Symposium University of Minnesota, Twin Cities Campus (Nov. 28, 2006).

Knothe, G. "Analytical Methods Used in the Production and Fuel Quality Assessment of Biodiesel," Transactions of the ASAE 2001, 44(2): 193-200.

Knothe, Gerhard et al., "Bidiesel: The Use of Vegetable Oils and Their Derivatives as Alternative Diesel Fuels," Oil Chemical Research, National Center for Agricultural Utilization Research, Agricultural Research Service, U.S. Department of Agriculture, Peoria, IL 61604 Unknown, 1-36.

(56) References Cited

OTHER PUBLICATIONS

Koh, Ashley D. "Non-Catalytic Biodiesel Production from Soybean Oil Using Supercritical Methanol," The 2006 Annual Meeting San Francisco, CA http://aiche.confex.com/aiche/2006/techprogram/P69978.HTM presented Nov. 15, 2006, 1.

Koscsisova, Teodora et al., "Hydrolysis of fatty acid in esters in subcritical water," Eur. J. Lipid Sci. Technol., vol. 108, 2006, pp. 652-658.

Kubatova, Alena et al., "Triacylglyceride Thermal Cracking: Pathways to Cyclic Hydrocarbons," Energy & Fuels, 2011,14 pages.

Kubicka, David et al., "Deactivation of HDS Catalysts in Deoxygenation of Vegetable Oils," Applied Catalysis A: General, vol. 394, 2011, pp. 9-17.

Kubicka, David et al., "Deoxygenation of Vegetable Oils over Sulfided Ni, Mo, and NiMo Catalysts," Applied Catalysis A: General, vol. 372, 2010, pp. 199-208.

Kulkarni, M. et al., "Waste Cooking Oil: An Economical Source for Biodiesel," Ind. Eng. Chem. Res. 2006, 45: 2901-2913.

Kulkarni, Mangesh G. et al., "Solid Acid Catalyxed Biodiesel Production by Simultaneous Esterification and Transesterification," Green Chem. 2006, 8: 1056-1062.

Kusdiana, Dadan et al., "Effects of water on biodiesel fuel production by supercritical methanol treatment," Bioresource Technology, vol. 91, 2004, pp. 289-295.

"Kyte Centrifuge Sales & Consulting," www.kcentrifuge.com, p. 1.

Lewkowitsch, J. "The Meaning of the Acetyl Value in fat Analysis," Chem. Zentr., vol. 1, 1899, pp. 375-376.

Li, Lixiong et al., "Catalytic Hydrothermal Conversion of Triglycerides to Non-ester Biofuels," Energy Fuels, vol. 24, 2010, pp. 1305-1315.

Li, Wei et al., "Study on Acyl Migration Kinetics of Partial Glycerides: Dependence on Temperature and Water Activity," Journal of Molecular Catalysis B: Enzymatic, vol. 63, 2010, pp. 17-22.

Liu, Yijun et al., "Transesterification of Poultry Fat with Methanol Using Mg—Al Hydrotalcite Derived Catalysts," Applied Catalysis A: General (Abstract only) 2007, vol. 331, 138-148.

Lopez, D.E. et al., "Transesterification of Triacetin with Methanol on Solid Acid and Base Catalysts," Appl. Catalysis A: General 2005, 295: 97-105.

Lopez, Dora E. et al., "Esterification and transesterification on tungstated zirconia: Effect of calcination temperature," Journal or Catalysis Apr. 1, 2007, vol. 247, Iss. 1, 43-50.

Lopez, Dora E. et al., "Esterification and transesterification using modified-zirconia catalysts," Applied Catalysis A: General, vol. 339, 2008, pp. 76-83.

Lotero, E. et al., "Synthesis of Biodiesel Via Acid Catalysis," Ind. Eng. Chem. Res. 2005, 44:5353-5363.

Lu, Jike et al., "Immobilized lipase *Candida* sp. 99-125 catalyzed methanolysis of glycerol trioleate: Solvent effect," Bioresource Technology, vol. 99, 2008, pp. 6070-6074.

Lusvardi, Victor S. et al., "The Effects of Bulk Titania Crystal Structure on the Adsorption and Reaction of Aliphatic Alcohols," Journal of Catalysis, vol. 153, 1995, pp. 41-53.

Ma, R et al., "Biodiesel Production: A Review," Bioresource Technol. 1999, 70:1-15.

Madsen, Anders T. et al., "Step Changes and Deactivation Behavior in the Continuous Decarboxylation of Stearic Acid," Ind. Eng. Chem. Res., vol. 50, 2011, pp. 11049-11058.

Maher, Kelly D. et al., "Pyrolytic Decarboxylation and Cracking of Stearic Acid," Ind. Eng. Chem. Res., vol. 47, 2008, pp. 5328-5336.

Martinez, Jose L. et al., "Effect of Water on Canola oil Hydrolysis in an Online Extraction-Reaction System Using Supercritical Co2," Ind. Eng. Chem. Res., vol. 41, 2002, pp. 6475-6481.

Mazzieri, V.M. et al., "Non-Catalytic Biodiesel Process with Adsorption-Based Refining," Fuel, vol. 90, 2011, pp. 1186-1196.

Mcneff, Clayton V. et al., "Continuous Production of 5-Hydroxymethylfurfural from Simple and Complex Carbohydrates," Applied Catalysis A: General, vol. 384, Issues 1-2, Aug. 2010, pp. 65-69.

Melero, Juan A. et al., "Acidic Mesoporous Silica for the Acetylation of Glycerol: Synthesis of Bioadditives to Petrol Fuel," Energy & Fuels 2007, 21: pp. 1782-1791.

Melero, Juan A. et al., "Production of Biofuels Via the Catalytic Cracking of Mixtures of Crude Vegetable Oils and Nonedible Animal Fats with Vacuum Gas Oil," Energy Fuels, vol. 24, 2010, pp. 707-717.

"Mexico Office Action," from MX Application No. MX/a/2009/008612, dated Jul. 11, 2012, (pp. 1-4) Including English translation, 4.

"Mexico Office Action," from MX Application No. MX/a/2009/008683, dated Oct. 10, 2012 (pp. 1-2) Including English translation.

Miller, Dennis J. et al., "Catalysis for Biorenewables Conversion," National Science Foundation Workshop Report www.egr.msu.edu/apps/nsfworkshop Apr. 2004, 1-63.

Minami, Eiji et al., "Kinetics of hydrolysis and methyl esterification for biodiesel production in two-step supercritical methanol process," Fuel, vol. 85, 2006, pp. 2479-2483.

Mittelbach, Martin et al., "Diesel Fuel Derived from Vegetable Oils, III. Emission Tests Using Methyl Esters of Used Frying Oil," JAOCS Jul. 1988, vol. 65, No. 7, 1185-1187.

Mohan, Dinesh et al., "Pyrolysis of wood/Biomass for Bio-Oil: A Critical Review," Energy and Fuels, vol. 20, 2006, pp. 848-889.

Moquin, Paul H. et al., "Kinetic modeling of hydrolysis of canola oil in supercritical media," Journal of Supercritical Fluids, vol. 45, 2008, pp. 94-101.

Moreau, C. et al., "Applied Catalysis A:General," vol. 145, No. 1-2, XP002454168 tables 1, 3 1996, pp. 211-224.

Murkute, Ambareesh D. et al., "Supported Mesoporous Solid Base Catalysts for Condensation of Carboxylic Acids," Journal of Catalysis, vol. 278, 2011, pp. 189-199.

Na, J. et al., "Hydrocarbon Production from Decarboxylation of Fatty Acid without Hydrogen," Catalysis Today, vol. 156, 2010, pp. 44-48.

Nawrocki, J. et al., "Chemistry of Zirconia and Its Use in Chromatography," J. Chromatog. 1993, A 657: 229-282.

"New Process Makes Diesel Fuel and Industrial Chemicals from Simple Sugar," College of Engineering University of Wisconsin—Madison, http://www.engr.wisc.edu/news/headlines/2006/Jun29a.html 1 of 3 Jun. 18, 2008 9:28 AM Jun. 29, 2006, pp. 1-3.

Ngaosuwan, Kanokwan et al., "Effect of solvent on hydrolysis and transesterification reactions on tungstated zirconia," Applied Catalysis A: General, vol. 380, 2010, pp. 81-86.

Ngaosuwan, Kanokwan et al., "Hydrolysis of Triglycerides Using Solid Acid Catalysts," Ind. Eng. Chem. Res, vol. 48, 2009, 4757-4767.

Ngaosuwan, Kanokwan et al., "Reaction Kinetics and Mechanisms for Hydrolysis and Transesterification of Triglycerides on Tungstated Zirconia," Top Catal, vol. 53, 2010, pp. 783-794.

"Non-Final Office Action," for Mexican Patent Application No. MX/a/2010/000135, dated Mar. 3, 2014 (2 pages).

"Notice of Allowance," for Canadian Patent Application No. 2660049, dated Mar. 23, 2015 (1 page).

"Notice of Allowance," from MX Application No. MX/a/2009/001280, corresponding to U.S. Appl. No. 60/821,498, dated May 3, 2011, (pp. 1-2), 2 Pgs.

O'connor, Charmian J. et al., "Determining the regio- and typo-selectivity of calf pregastric lipase," Journal of Molecular Catalysis B: Enzymatic, vol. 16, 2001, pp. 147-157.

"Office Action," for CA Application No. 2660049, dated May 8, 2014 (2 pages).

"Office Action," for Canadian Patent Application No. 2,691,545, dated Jan. 31, 2014 (2 pages).

"Office Action," for Canadian Patent Application No. 2,765,043, dated May 18, 2016 (4 pages).

"Office Action," for Mexican Application No. MX/a/2011/013275, dated Jun. 19, 2013 (4 pages).

"Office Action," from CA Application No. 2660049, dated Jun. 28, 2013, 2 pages.

Omota, F. et al., "Fatty Acid Esterification by Reactive Distillation: Part 2—Kinetics-based Design for Sulphated Zirconia Catalysts," Chemical Engineering Science 2003, 58: 3175-3185.

(56) References Cited

OTHER PUBLICATIONS

Ondrey, G. "Biodiesel Production Using a Heterogeneous Catalyst," Chemical Engineering 2004, 111(11):13.
Ooi, Yean Sang et al., "Catalytic Cracking of Used Palm Oil and Palm Oil Fatty Acids Mixture from the Production of Liquid Fuel: Kinetic Modeling," Energy & Fuels, vol. 18, 2004, pp. 1555-1561.
Otera, J. "Transesterification," Chem. Rev. 1993, 93:1449-1470.
Palanisamy, Shanmugam et al., "Thermal Treatment of Rapeseed Oil," Bioenergy Technology, 2011, pp. 546-551.
Pariente, Stephane et al., "Etherification of glycerol with ethanol over solid acid catalysts," 2008, Green Chem., 11, 1256-1261.
Parve, Omar et al., "Lipase-Catalysed Enantioselective Hydrolysis: Interpretation of the Kinetic Results in Terms of Frontier Orbital Localisation," Tetrahedron, vol. 53, 1997, pp. 4889-4900.
Patel, Akshay D. et al., "Techno-Economic Analysis of 5-Nonanone Production from Levulinic Acid," Chemical Engineering Journal, vol. 1, 2010, pp. 311-321.
"PCT International Search Report and Written Opinion," for International Application No. PCT/US2010/038000 corresponding to U.S. Appl. No. 12/797,393, dated Oct. 4, 2010, pp. 1-13.
"PCT International Search Report and Written Opinion," from International Application No. PCT/US2008/068188, corresponding to U.S. Appl. No. 12/146,175, dated Sep. 3, 2008, pp. 1-15.
"PCT International Search Report and Written Opinion," PCT International Search Report and Written Opinion from International Application No. PCT/US2008/053844, corresponding to U.S. Appl. No. 12/030,649, dated Aug. 6, 2008, pp. 1-14.
"PCT Notification Concerning Transmittal of International Preliminary Report on Patentability from International Application No. PCT/US2009/069280, corresponding to U.S. Appl. No. 12/645,119, dated Jul. 7, 2011,," pp. 1-12, 12 pgs.
"PCT Notification Concerning Transmittal of International Preliminary Report on Patentability," From International Application No. PCT/US2007/075211, corresponding to U.S. Appl. No. 11/833,839, dated Feb. 19, 2009, pp. 1-9.
"PCT Notification Concerning Transmittal of International Preliminary Report on Patentability," from International Application No. PCT/US2008/053844, corresponding to U.S. Appl. No. 12/030,649, dated Aug. 27, 200.
"PCT Notification Concerning Transmittal of International Preliminary Report on Patentability," from International Application No. PCT/US2008/068188, corresponding to U.S. Appl. No. 12/146,175, dated Jan. 14, 2010, pp. 1-5.
"PCT Notification Concerning Transmittal of International Preliminary Report on Patentability," From International Application No. PCT/US2008053883, corresponding to U.S. Appl. No. 12/030,801, dated Aug. 27, 2009, pp. 1-9.
"PCT Notification Concerning Transmittal of International Preliminary Report on Patentability," from International Application No. PCT/US2010/38000, corresponding to U.S. Appl. No. 61/185,453, dated Dec. 22, 2011, pp. 1-6.
Pei, Z. F. et al., "On the Intermediates of the Acetic Acid Reactions on Oxides: An IR Study," Applied Surface Science, vol. 103, 1996, pp. 171-182.
Perlack, Robert D. et al., "Biomass as Feedstock for Bioenergy and Bioproducts Industry: Technical Feasibility of a Billion-Ton Annual Supply," U.S. Department of Agriculture Apr. 2005, 1-78.
Peterson, Andrew A. et al., "Thermochemical Biofuel Production in Hydrothermal Media: A Reivew of Sub- and Supercritical Water Technologies," Energy and Environmental Science, 2008, 1, pp. 32-65.
Peterson, C. L. et al., "Continuous Flow Biodiesel Production," Appl. Eng. Agricul. 2002, 18: 5-11.
Petkewich, Rachel "Sweet Routes to Sustainability: Catalytic reactions converts sugars from biomass into renewable fuel and feedstock," Cnemical & Engineering News, http://pubs.acs.org/cen/news/85/i26/8526notw1.html Jun. 25, 2007, V. 85, No. 26, p. 8.
Pinto, A. C. et al., "Biodiesel: An Overview," J. Braz. Chem. Soc. 2005, 16: 1313-1330.
Piyatheerawong, Weera et al., "Enzymatic Preparation of Enantiomerically Pure sn-2, 3-Dicylglycerols: A Stereoselective Ethanolysis Approach," JAOCS, vol. 83, 2006, pp. 603-607.
Priecel, Peter et al., "The Role of Ni Species in the Deoxygenation of Rapeseed Oil Over NiMo-Alumina Catalysts," Applied Catalysis A: General, vol. 397, 2011, 127-137.
Pruszko, R. "Strategic Biodiesel Decisions," Iowa State University—University Extension CIRAS 2006, 1-32.
Qi, Zhang et al., "Review of bioMass Pyrolysis Oil Properties and Upgrading Research," Energy Conversion and Management vol. 48, 2007, pp. 87-92.
Qi., X. et al., "Catalysis Communications," vol. 9, No. 13, XP022824415 p. 2245, paragraph 2.2; tables 1-3,table 2 Jul. 20, 2008, pp. 2244-2249.
"Qualitative and Quantitative Analysis in GC and GCMS," Customer Support Centre, Shimadzu Asia Pacific Pte. Ltd., 2006, Singapore (32 pages).
Quirino, Rafael L. et al., "Studying the Influence of Alumina Catalysts Doped with Tin and Zinc Oxides in the Soybean Oil Pyrolysis Reaction," J AM Oil Chem Soc, vol. 86, 2009, pp. 167-172.
Raddi De Araujo, Lucia R. et al., "H3PO4/Al2O3 Catatysts: Characterization and Catalytic Evaluation of Oleic Acid Conversion to Biofuels and Biolubricant," Materials Research 2006, vol. 9, No. 2, 181-184.
Reisch, Marc S. "Start-up Firms Pursue Biofuels," Chemical & Engineering News Nov. 20, 2006, vol. 84, No. 47, 1-2(web).
Renz, Michael "Ketonization of Carboxylic Acids by Decarboxylation: Mechanism and Scope," Eur. J. Org. Chem., 2005, pp. 979-988.
"Response to Mexico Office Action," dated Oct. 30, 2012 for MX Application No. MX/a/2009/008612 8 pages.
"Response to Office Action," for Canadian Patent Application No. 2,660,049, dated May 8, 2014 and filed with the CIPO Nov. 6, 2014 (5 pages).
Rigney, M. P. et al., "Physical and Chemical Characterization of Microporous Zirconia," J. Chromatog 1990, 499: 291-304.
Robichaud, et al., "An Improved Oil Emulsion Synthesis Method for Large, Porous Zirconia Particles for Packed-or Fluidized-Bed Protein Chromatography," Sep. Science Technol., 32(15):2547-2559 (1997).
Ruan, Roger et al., "Size matters: small distributed biomass energy production systems for economic viability," Int J Agric & Biol Eng Aug. 2008, vol. 1 No. 1, pp. 64-68.
Saka, Shiro et al., "Useful Products from Lignocellulosics by Supercritical Water Technologies," The 2nd Joint International Conference on "Sustainable Energy and Environment (SEE 2006)," Nov. 2006, 5 pages.
Sassi, "Methanol to hydrocarbon catalysis on sulfated zirconia proceeds through a hydrocarbon-pool mechanism," Catalysis Letters, 81(1-2):101-105 (2002).
Schmid, U. et al., "Highly Selective Synthesis of 1,3-Oleoyl-2-Palmitoylglycerol by Lipase Catalysis," Biotechnology and Bioengineering, vol. 64, 1999, pp. 678-684.
Schuchardt, Ulf et al., "Transesterification of Vegetable Oils: a Review," J. Braz. Chem. Soc. 1998, vol. 9, No. 1, 199-210.
Serrano-Ruiz, Juan Carlos et al., "Catalytic Upgrading of Lactic Acid to Fuels and Chemicals by Dehydrations/Hydrogenation and C-C Coupling Reactions," Green Chem., vol. 11, 2009, pp. 1101-1104.
Serrano-Ruiz, Juan Carlos et al., "Catalytic Upgrading of Levulinic Acid to 5-Nonanone," Green Chem., vol. 12, 2010, pp. 574-577.
Serrano-Ruiz, Juan Carlos et al., "Transformation of Biomass-Derived Platform Molecules: From High Added-Value Chemicals to Fuels Via Aqueous-Phase Processing," Chemical Society Reviews, vol. 40, pp. 5266-5281.
Shanks, Brent H. "Conversion of Biorenewable Feedstocks: New Challenges in Heterogeneous Catalysis," Ind. Eng. Chem. Res., vol. 49, 2010, pp. 10212-10217.
Shieh, Chwen-Jen et al., "Optimized Enzymatic Synthesis of Geranyl Butyrate with Lipase AY from Candida Rugosa," Biotechnology and Bioengineering, vol. 51, 1996, pp. 371-374.

(56) References Cited

OTHER PUBLICATIONS

Silva, Lisa et al., "Colorado Diesel School Bus Retrofit Program," A Cooperative Effort of the Regional Air Quality Council and the Colorado Department of Public Health and Environment 2006, 1-17.
Simonetti, Dante A. et al., "Catalytic Production of Liquid Fuels from Biomass-Derived Oxygenated Hydrocarbons: Catalytic Coupling at Multiple Length Scales," Catalysis Reviews, vol. 51, 2009, pp. 441-484.
Siswanto, Dessy Y. et al., "Gasoline Production from Palm Oil Via Catalytic Cracking Using MCM-41: Determination of Optimum Condition," Journal of Engineering and Applied Sciences, vol. 3, 2008, pp. 42-46.
Stefanidis, S.D. et al., "In-Situ Upgrading of Biomass Pyrolysis Vapors: Catalyst Screening on a Fixed Bed Reactor," Bioresource Technology, vol. 102, 2011, pp. 8261-8267.
Steinbusch, Kirsten J. et al., "Biological Formation of Caproate and Caprylate from Acetate: Fuel and Chemical Production from Low Grade Biomass," Energy Environ. Sci., vol. 4, 2011, p. 216.
Su, Yu et al., "Single Step Conversion of Cellulose to 5-hydroxymethylfurfural (HMF), A Versatile Platform Chemical," Applied Catalysis A: General, 361 Apr. 9, 2009, 117-122.
Suib, Steven L. "New and Future Developments in Catalysis," Catalytic Biomass Conversion, p. 184, ISBN: 978-0-444-53878-9.
Suppes, G. J. et al., "Transesterification of Soybean Oil with Zeolite and Metal Catalysts," Applied Catalysis A: General 2004, 257: 213-223.
Suwannakarn, Kaewta et al., "A comparative study of gas phase esterification on solid acid catalysts," Catalysis Letters Apr. 2007, vol. 114, Nos. 3-4, 1-7.
Swaminathan, R. et al., "Studies on the Ketonization of Acetic Acid on Chromia: II. The Surface Reaction," Journal of Catalysis, vol. 16, 1970, pp. 357-362.
Takahashi, Yoshinori et al., "Characteristics of Lipase Modified with Water-soluble Acylating Reagents and Its Esterification Ability," Biosci. Biotech. Biochem., vol. 59, 1995, pp. 809-812.
Tamunaidu, Pramila et al., "Catalytic Cracking of Palm Oil for the Production of Biofuels: Optimization Studies," Bioresource Technology, vol. 98, 2007, pp. 3593-3601.
Tanksale, Akshat et al., "A Review of catalytic Hydrogen production Processes from Biomass," Renewable and Sustainable Energy Reviews, vol. 14, 2010, pp. 166-182.
Tanner, R.E. et al., "Structure and Chemical Reactivity of Adsorbed Carboxylic Acids on Anatase $TiO_2(001)$," Surface Science, vol. 506, 2002, pp. 251-271.
Tavakoli, Omid et al., "Squid Oil and Fat Production from Squid Wastes Using Subcritical Water Hydrolysis: Free Fatty Acids and Transesterification," Ind. Eng. Chem. Res., vol. 45, 2006, pp. 5675-5680.
Ten Dam, Jeroen et al., "Renewable Chemicals: Dehydroxylation of Glycerol and Polyols," ChemSusChem, vol. 4, 2011, pp. 1017-1034.
Toor, Saqib S. et al., "Hydrothermal Liquefaction of Biomass: A Review of Subcritical Water Technologies," Energy 36 (2011), pp. 2328-2342.
Trentin, Claudia M. et al., "Continuous Catalyst-Free Production of Fatty Acid Ethyl Esters from Soybean Oil in Microtube Reactor using Supercritical Carbon Dioxide as Co-Solvent," J. of Supercritical Fluids 56 (2011) 283-291 (9 pages).
Trentin, Claudia M. et al., "Continuous Production of Soybean Biodiesel with Compressed Ethanol in a Microtube Reactor using Carbon Dioxide as Co-Solvent," Fuel Processing Technology 92 (2011) 952-958 (7 pages).
Twaiq, Farouq A. et al., "Liquid Hydrocarbon Fuels from Palm Oil by Catalytic Cracking Over Aluminosilicate Mesoporous Catalysts with Various Si/Al ratios," Microporous and Mesoporous Materials, vol. 64, 2003, pp. 95-107.

Tyson, K. S. "Brown Grease Feedstocks for Biodiesel," National Renewable Energy Laboratory Jun. 19, 2002, 1-34.
Ulgen, Arda et al., "Conversion of Glycerol to Acrolein in the Presence of $WO_3/TiO_2$ Catalysts," Applied Catalysis A; General 400 (2011) pp. 34-38.
Unknown, "AMBERLITEtm FP Ion Exchange Resins," Amberlite FP technical bulletin http://www.advancedbiosciences.com Dec. 2004, 1-7.
Unknown, "Standard Test Method for Acid Number of Petroleum Products by Potentiometric Titration," ASTM International, Designation: D664-04 Mar. 2004, 1-7.
Unknown, et al., "Oak Ridge lab develops materials for biodiesel catalysis," Biodiesel Magazine http://biodieselmagazine.com/article-print.jsp?article_id=1580 2007, 1.
Van Tol, J. B. et al., "Do Organic Solvents Affect the Catalytic Properties of Lipase? Intrinsic Kinetic Parameters of Lipases in Ester Hydrolysis and Formation in Various Organic Solvents," Biotechnology and Bioengineering, vol. 47, 1995, pp. 71-81.
Varma, Mahesh N. et al., "Effect of Chain Length on Enzymatic Hydrolysis of p-Nitrophenyl Esters in Supercritical Carbon Dioxide," Appl Biochem Biotehnol, vol. 144, 2008, pp. 213-223.
Verkade, J. G. et al., "Nanoporous Solid Catalysts for Conversion of Soybean Oil to Biodiesel," Center for Catalysis, Iowa State University http://www.iprt.iastate.edu/ccat/nano.html Feb. 22, 2006, 1-4.
Vieitez, Ignacio et al., "Continuous catalyst-free methanolysis and ethanolysis of soybean oil under supercritical alcohol/water mixtures," Renewable Energy, vol. 35., 2010, pp. 1976-1981.
Vieitez, Ignacio et al., "Continuous Production of Soybean Biodiesel in Supercritical Ethanol-Water Mixtures," American Chemical Society, Energy & Fuels Jun. 17, 2008, pp. 1-5.
Vivier, Laurence et al., "Ceria-Based Solid Catalysts for Organic Chemistry," ChemSusChem, vol. 3, 2010, pp. 654-678.
Vonghia, Enrico et al., "Pathways for the Deoxygenation of Triglycerides to Aliphatic Hydrocarbons over Activated Alumina," Energy & Fuels, vol. 9, 1995, pp. 1090-1096.
Watanabe, et al., Carbohydrate Research 340 (2005) 2005, 1925-1930.
Watanabe, Masaru et al., "Catalytic Hydrogen Generation from Biomass (Glucose and Cellulose) with $ZrO_2$ in Supercritical Water," Biomass and Bioenergy 2002, 22, 405-410.
White, D. H. et al., "Development of an Extruder-Feeder Biomass Direct Liquefactoin Process," Final Report, vol. 1, Oct. 1991, Parts 1-3, 294 pages.
White, Don H. et al., "Biomass Liquefaction Utilizing Extruder-Feeder Reactor System," Department of Chemical Engineering, University of Arizona, date unknown, pp. 106-116.
Wiggers, et al., "Biofuels from continuous fast pyrolysis of soybean oil: A pilot plant study," Bioresource Technology, vol. 100, (2009) pp. 6570-6577.
Xie, W. et al., "Synthesis of Biodiesel from Soybean Oil Using Heterogeneous KF/ZnO Catalyst," Catalyst Letters Feb. 2006, 107: 53-59.
Xu, M. et al., "Synthesis of Dimethyl Ether (DME) from Methanol Over Solid-Acid Catalysts," Applied Catalysis A: General 149,, Elsevier, Science, Amsterdam, NL, vol. 149, No. 2, pp. 289-301 Feb. 6, 1997.
Yalpani, M. "Alterations of Polysaccharide Intergrity and Electro-chemical Modifications," Polysaccharides. Syntheses, Modifications and Structure Jan. 1, 1988, 370-4004.
Yamakawa-Kobayashi, Kimiko et al., "Relation of the −514C/T Polymorphism in the Hepatic Lipase Gene to Serum HDL and LDL Cholesterol Levels in Postmenopausal Women Under Hormone Replacement Therapy," Atherosclerosis, vol. 162, 2002, pp. 17-21.
Yared, Ivan et al., "Modeling of Liquid hydrocarbon Fuel Production from Palm Oil Via Catalytic Cracking Using MCM-41 as Catalyst," Journal of Engineering and Applied Sciences, vol. 3, 2008, pages.
Yean Sang, Ooi "Biofuel Production from Catalytic Cracking of Palm Oil," Energy Sources, vol. 25, 2003, pp. 859-869.
Yokoyama, Shin-Ya et al., "Liquid Fuel Production from Ethanol Fermentation Stillage," Chemistry Letters 1986, pp. 649-652.

(56) References Cited

OTHER PUBLICATIONS

Yu, Fei et al., "Liquefaction of Corn Cobs with Supercritical Water Treatment," American Society of Agricultural and Biological Engineers 2007, vol. 50(1): 175-180.
Yu, Fei et al., "Liquefaction of Corn Stover and Preparation of Polyester from the Liquefied Polyol," Applied Biochemistry and Biotechnology 2006, vol. 129-132, pp. 574-585.
Yu, Fei et al., "Physical and Chemical Properties of Bio-Oils From Microwave Pyrolysis of Corn Stover," Applied Biochemistry and Biotechnology 2007, vol. 136-140, pp. 957-970.
Yu, Fei et al., "Reaction Kinetics of Stover Liquefaction in Recycled Stover Polyol," Applied Biochemistry and Biotechnology 2006, vol. 129-132 pp. 563-573.
Yu, Yang et al., "Enzymatic Synthesis of Feruloyated Lipids: Comparison of the Efficiency of Vinyl Ferulate and Ethyl Ferulate as Substrates," J Am Oil Chem Soc, vol. 87, 2010, pp. 1443-1449.
Zhang, P. "A New Process for Biodiesel Production Based on Waste Cooking Oils and Heterogeneous Catalysts," USDA-SBIR Agreement #2005-33610-15497 2005, 1-2.
Zheng, Yang et al., "Dual Response Surface-Optimized Process for Feruloylated Diacylglycerols by Selective Lipase-Catalyzed Transesterification in Solvent Free System," Bioresource Technology, vol. 100, 2009, pp. 2896-2901.

METHODS AND APPARATUS FOR PRODUCING ALKYL ESTERS FROM LIPID FEED STOCKS, ALCOHOL FEEDSTOCKS, AND ACIDS

This application claims the benefit of U.S. Provisional Application No. 62/627,511, filed Feb. 7, 2018, the content of which is herein incorporated by reference in its entirety.

FIELD

Embodiments herein relate to the production of alkyl esters from lipid feed stocks. More specifically, embodiments herein relate to methods and apparatus for producing alkyl esters from lipid feedstocks in a reaction mixture containing an alcohol, carbon dioxide ($CO_2$), carbon monoxide (CO), and/or one or more acids, and a metal oxide catalyst.

BACKGROUND

Biodiesel is a processed fuel derived from biological sources such as plant oils and/or animal fats. Biodiesel can be utilized alone or mixed with conventional petroleum-based diesel for use in most standard diesel engines. Biodiesel can also be utilized as a heating fuel in commercial and domestic boilers.

Biodiesel can be considered an environmentally friendly alternative to petroleum-based fossil fuels. For example, use of biodiesel can result in an overall reduction in greenhouse gas emissions and can be produced domestically, resulting in a lower dependence on fossil fuel imports.

Biodiesel can contain one or more long-chain fatty acid alkyl esters, including, but not limited to, fatty acid methyl esters, fatty acid ethyl esters, fatty acid propyl esters and fatty acid isopropyl esters formed from a transesterification or esterification reaction. Fatty acid alkyl esters can be created from the transesterification of triglycerides present in plant oil feedstocks and/or animal fat feedstocks. Fatty acid alkyl esters can also be created from the esterification of free fatty acids present in such feedstocks. The conversion to fatty acid alkyl esters can be produced by catalyzed or uncatalyzed reactions.

SUMMARY

Embodiments herein relate to the production of alkyl esters from lipid feed stocks. More specifically, embodiments herein relate to methods and apparatus for producing alkyl esters from lipid feedstocks in a reaction mixture with an alcohol, $CO_2$, CO, and/or one or more acids, and a metal oxide catalyst.

In an embodiment, a process for producing alkyl esters is provided. The process can include mixing a lipid feed stock with an alcohol and at least one of carbon dioxide and/or one or more acids to form a reaction mixture and contacting the reaction mixture with a catalyst under supercritical conditions for the alcohol, the catalyst including a metal oxide.

In some embodiments, the metal oxide catalyst can be selected from the group including alumina, titania, zirconia, and hafnia.

In some embodiments, the metal oxide catalyst can include an unmodified metal oxide including alumina, titania, zirconia, or hafnia.

In some embodiments, the metal oxide catalyst can include titania.

In some embodiments, the carbon dioxide can be present in an amount equal to at least 0.1 wt. percent of the mass of the alcohol added.

In some embodiments, the lipid feed stock can include a component selected from the group including acidulated soapstock, tall oil, rapeseed oil, soybean oil, canola oil, cottonseed oil, grape seed oil, mustard seed oil, corn oil, linseed oil, sunflower oil, poppy-seed oil, walnut oil, peanut oil, rice bran oil, *camellia* oil, castor oil, and olive oil, palm kernel oil, coconut oil, rice oil, algae oil, seaweed oil, Chinese Tallow tree oil, yellow grease, choice white grease, lard, tallow, brown grease, fish oil and poultry fat.

In some embodiments, the lipid feed stock can have an acid number of greater than or equal to 3 mg KOH/g oil.

In some embodiments, the process can further include the step of contacting the reaction mixture with a catalyst including the conversion of the lipid feed stock from an acid number of equal to 3 mg KOH/g oil to an acid number of less than or equal to 0.5 mg KOH/g oil.

In some embodiments, the process can further include the addition of an organic acid, a Bronsted acid, or an inorganic acid to the reaction mixture.

In some embodiments, the process can further include mixing an inorganic base or an organic base into the reaction mixture.

In some embodiments of the process, the step of contacting the reaction mixture with a catalyst can be performed at a temperature of between 200 and 400 degrees Celsius.

In some embodiments of the process, the step of contacting the reaction mixture with a catalyst can be performed at a pressure of between 1000 and 5000 psi.

In some embodiments of the process, contacting the reaction mixture with a catalyst can be performed with a residence time of less than 60 seconds.

In some embodiments of the process, a catalyst having particles with an average particle size of 0.2 microns to 2 millimeters can be used.

In some embodiments of the process, a catalyst with a porosity of between 0.3 and 0.6 can be used.

In some embodiments of the process, a catalyst with a pore volume of between 0 and 0.6 ml/gram can be used.

In some embodiments of the process, a particulate metal oxide with a surface area of between 1 and 200 $m^2$/gram can be used.

In some embodiments of the process, a C1-C6 alcohol, such as methanol or ethanol, can be used.

In some embodiments, the process can further include the step of removing residual free fatty acids from the reaction mixture.

In some embodiments, the process can further include removing residual free fatty acids from the reaction mixture by adding dimethyl carbonate to the reaction mixture.

In some embodiments, the process can further include removing residual free fatty acids from the reaction mixture by adsorbing the free fatty acids to a metal oxide substrate and separating the reaction mixture from the metal oxide substrate.

In some embodiments, the process can further include the production of an amount of alkyl esters that is at least 10% by weight greater than that produced by an otherwise identical reaction mixture lacking the carbon dioxide and/or one or more acids under the same reaction conditions and residence time.

In another embodiment, a process for producing alkyl esters is provided. The process can include mixing a lipid feed stock with an alcohol and an acid to form a reaction mixture, the acid including carbonic acid and/or one or more organic acids. The process can also include contacting the reaction mixture with a catalyst under supercritical conditions for the alcohol, the catalyst including a metal oxide selected from the group consisting of alumina, titania, zirconia, and hafnia, where the metal oxide has been pretreated with a Bronsted acid or a Bronsted base.

In some embodiments, the process can include the use of a metal oxide that has been pretreated with a Bronsted acid, including but not limited to hydrobromic acid, hydrochloric acid, hydroiodic acid, nitric acid, sulfuric acid, perchloric acid, boric acid, chloric acid, phosphoric acid, pyrophosphoric acid, methanethiol, chromic acid, permanganic acid, phytic acid and ethylenediamine tetramethyl phosphonic acid (EDTPA).

In an embodiment, a process producing alkyl esters via transesterification or esterification from a feed stock is provided. The process can include mixing a lipid feed stock with an alcohol and an acid form a reaction mixture, the feed stock including a triglyceride and/or a carboxylic acid and the acid including carbon dioxide and/or one or more organic acids. The process can also include pumping the reaction mixture into a housing including a porous catalyst such that the reaction mixture comes into contact with the porous catalyst. The porous catalyst can have an average particle size of 0.2 microns to 1 millimeter. The temperature and pressure within the housing can be set to supercritical conditions for the alcohol. In some embodiments, the porous catalyst can include a metal oxide such as one or more of alumina, titania, zirconia, and hafnia. The process can further include collecting a reaction product from the housing, where the reaction product can include esters in an amount at least equal to 80% of the triglyceride or carboxylic acid in the feed stock on a molar basis.

In an embodiment, a process for producing alkyl esters is provided. The process can include mixing a lipid feed stock with an alcohol and at least one of carbon monoxide or one or more acids to form a reaction mixture and contacting the reaction mixture with a catalyst under supercritical conditions for the alcohol, where the catalyst can include a metal oxide.

In some embodiments of the process, carbon monoxide can be present in an amount equal to at least 0.1 wt. percent of the mass of the alcohol added.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As discussed above, biodiesel formed from one or more long-chain fatty acid alkyl esters, can be created by the transesterification or esterification of lipid feedstocks. The transesterification and esterification reactions can be catalyzed under homogeneous or heterogeneous reaction conditions.

Without wishing to be bound by any particular theory, it is believed that the addition of carbon dioxide ($CO_2$) and/or carbon monoxide (CO) to the reaction mixture can further catalyze the transesterification and esterification of lipid feedstocks into biodiesel fuels. It is also believed that addition of $CO_2$ and/or CO can further drive the transesterification and esterification reactions to completion. In some cases, the acid number can be less than 0.5 (mg KOH/g oil) and specifically as close to 0 (mg KOH/g oil) as possible.

Figure 1:
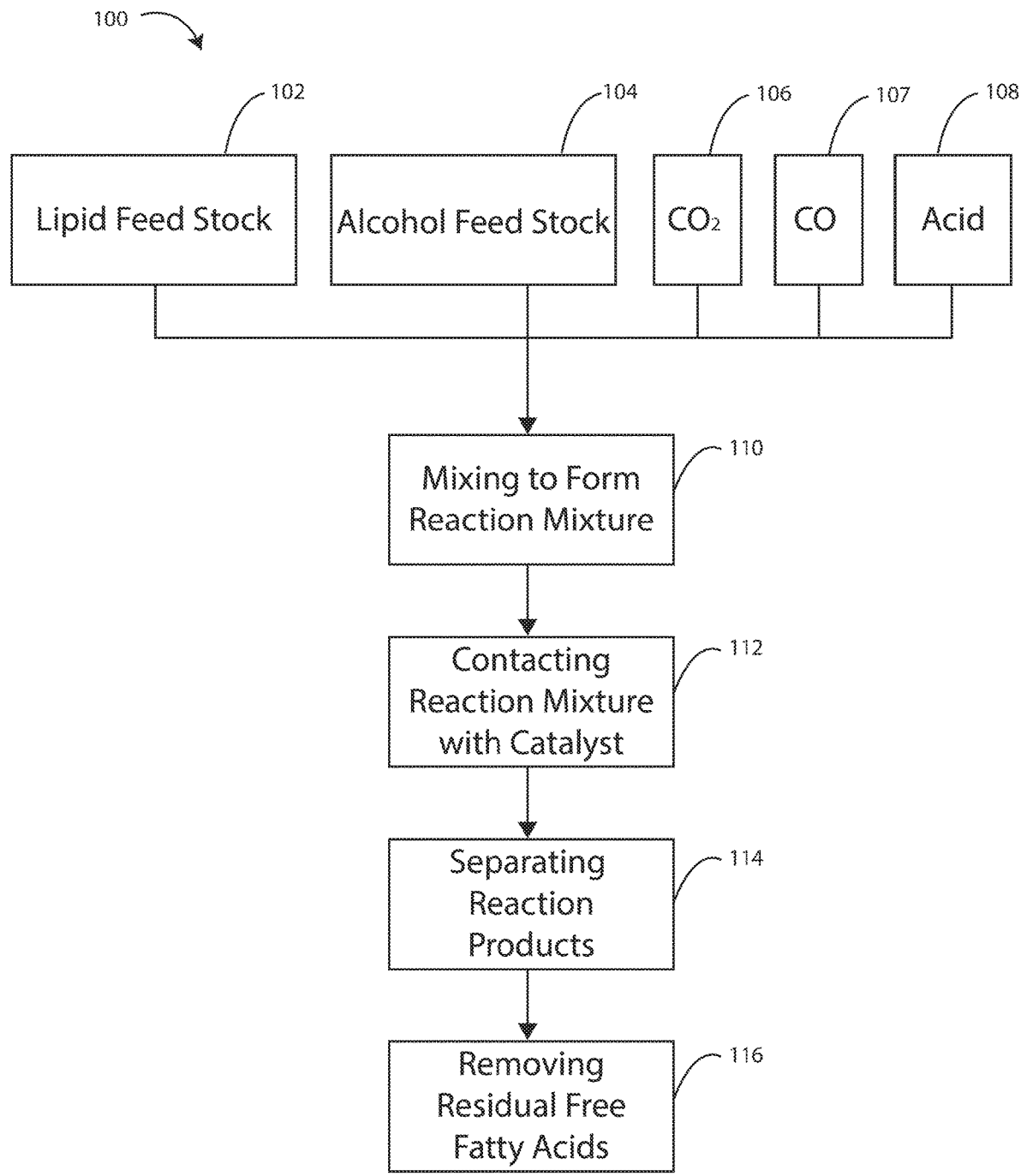
FIG. 1 is a schematic view of an exemplary process in accordance with the embodiments herein.

Referring now to FIG. 1, a schematic view of an exemplary process 100 for producing alkyl esters is shown. The process can begin with mixing together a lipid feed stock 102, an alcohol feed stock 104, and at least one of $CO_2$ 106, CO 107, and/or one or more acids 108 to form a reaction mixture at 110. It will be appreciated that in some cases the process can begin with mixing together a lipid feed stock 102, an alcohol feed stock 104, and $CO_2$ 106. In some embodiments, the process can begin with mixing together a lipid feed stock 102, an alcohol feed stock 104, and one or more acids 108. In yet other embodiments, the process can begin with mixing together a lipid feed stock 102, and alcohol feed stock 104, $CO_2$ 106, and one or more acids 108. In some embodiments, the process can begin with mixing together a lipid feed stock 102, an alcohol feed stock 104, and CO 107. In yet other embodiments, the process can begin with mixing together a lipid feed stock 102, and alcohol feed stock 104, CO 107, and one or more acids 108.

It will be appreciated that in some embodiments the reaction mixture can contain an amount of water suitable to react with $CO_2$ gas to form carbonic acid. Without wishing to be bound by any particular theory, it is believed that $CO_2$ gas dissolves in water to form carbonic acid ($H_2CO_3$) as follows:

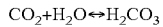

$$CO_2 + H_2O \leftrightarrow H_2CO_3$$

The amount of water suitable for use herein can include the addition of greater than or equal to 0.05% by weight (by wt.) water added to the reaction mixture. In some embodiments, the amount of water added to the reaction mixture can include 0.05% by wt., 0.1% by wt., 0.5% by wt., 1.0% by wt., 1.5% by wt., 2% by wt., 3% by wt., 4% by wt., 5% by wt., or 10% by wt. It will be appreciated that amount of water added to the reaction mixture can fall within a range, wherein any of the forgoing weight percentages can serve as the lower or upper bound of the range, provided that the lower bound of the range is a value less than the upper bound of the range. It will be appreciated that in some embodiments, gaseous $CO_2$ can first be passed through water to form carbonic acid and then mixed into the reaction mixture. In other cases, the $CO_2$ can be added to the reaction mixture once it reaches the reactor 334, as will be discussed further below in reference to FIG. 3. In some embodiments, the water can be introduced into the reaction mixture as a component of the alcohols used herein.

It will be appreciated that in some embodiments the reaction mixture can contain an amount of water suitable for reaction with CO to form $CO_2$ at the high temperatures and pressures used in the reactions herein. In some cases, CO can be added directly to the reaction mixture. In other cases, the CO can be added to the reaction mixture once it reaches the reactor 334, as will be discussed further below in reference to FIG. 3. Without wishing to be bound by any particular theory, it is believed that CO can react with water vapor at high temperatures to form carbon dioxide and hydrogen gases.

The lipid feed stock 102 can include various types of plant oils and animal fats as described more fully below. The alcohol feed stock 104 can include one or more types of alcohol as described more fully below. The one or more acids 108 can include one or more types of acids as described more fully below. In some embodiments, one or more lipid feed stocks, one or more alcohol feed stocks, $CO_2$ and/or CO are mixed together to form a reaction mixture. In other embodiments, one or more lipid feed stocks, one or more alcohol feed stocks, and one or more acids are mixed together to form a reaction mixture. In yet other embodiments, one or more lipid feed stocks, one or more alcohol feed stocks, $CO_2$, CO, and/or one or more acids are mixed together to form a reaction mixture.

Mixing the separate components to form a reaction mixture can be done in a separate mixing vessel relative to the vessel containing the separate components, or it can be done by simply injecting one component at a time into the other components until all components are combined. In some embodiments, the amount of alcohol supplied can be in a molar excess to the stoichiometric ratio of the reaction. By way of example, for the transesterification of a triglyceride, the stoichiometric ratio is 3 moles of alcohol for every 1 mole of triglyceride. However, the reaction can be pushed farther towards completion by adding a molar excess of alcohol.

Accordingly, in an embodiment, an amount of alcohol can be added to the reaction mixture that exceeds the ratio of 3 parts alcohol to 1 part triglyceride. For example, in some embodiments, the amount of alcohol added to the reaction mixture can be 4 parts alcohol to 1 part triglyceride. In some embodiments, the amount of alcohol added to the reaction mixture can be 5 parts alcohol to 1 part triglyceride. In some embodiments, the amount of alcohol added to the reaction mixture can be 6 parts alcohol to 1 part triglyceride. However, in other embodiments the alcohol can be added to the reaction mixture in a less than stoichiometric ratio. For example, in some embodiments, the reaction mixture can have a ratio of 1-3 moles of alcohol to 1 mole of triglyceride.

Similarly, the reaction can be pushed even farther towards completion by adding $CO_2$ and/or one or more acids to catalyze the esterification of free fatty acids in the reaction mixture. Without wishing to be bound by theory, it is believed that the addition of $CO_2$ to the reaction mixture can result in the formation of carbonic acid ($H_2CO_3$) due to the reaction between $CO_2$ and water present in the reaction mixture. Carbonic acid and/or one or more additional acids can catalyze the esterification of free fatty acids or otherwise enhance the conversion of free fatty acids to esters.

In some embodiments, the process can include mixing $CO_2$ into the reaction mixture in an amount equal to at least 0.1 weight percent (wt. percent or wt. %) of the mass of the alcohol added. In some embodiments, the process can include adding $CO_2$ in an amount equal to at least 1.0 wt. percent of the mass of the alcohol added. In some embodiments, the process can include adding $CO_2$ in an amount equal to at least 0.1 wt. %, 0.5 wt. %, 1.0 wt. %, 2 wt. %, 3 wt. %, 4 wt. %, 5 wt. %, 6 wt. %, 7 wt. %, 8 wt. %, 9 wt. %, 10 wt. %, 15 wt. %, 20 wt. %, 25 wt. %, 30 wt. %, 40 wt. %, or 50 wt. % of the mass of the alcohol added. In some embodiments, an amount of $CO_2$ can be added to achieve maximum $CO_2$ solubility in water at the temperatures and pressures suitable for use in the reactions described herein. In some embodiments, the reaction mixture can contain carbonic acid at a concentration of at least 0.05, 0.1, 0.25, 0.5, 0.75, 1, 1.5, 2, 3, 4, 5, 7.5, 10, 15 or 20 M, or can have a concentration falling within a range between any of the foregoing.

The pH of the reaction mixture can vary. In some embodiments, the pH can be about 0.5, 1, 2, 3, 4, 5, 6, 7, 8, 9, 10, 11, 12, 13 or 13.5, or the pH can fall within a range between any of the foregoing. In some embodiments, the pH of the reaction mixture can be acidic. In some embodiments, the pH of the reaction mixture can be less than 7. In some embodiments, the pH of the reaction mixture can be less than 3. In some embodiments, the pH of the reaction mixture can be from about 2 to about 4.

In some embodiments, the process can include mixing CO into the reaction mixture in an amount equal to at least 0.1 weight percent (wt. percent or wt. %) of the mass of the alcohol added. In some embodiments, the process can include adding CO in an amount equal to at least 1.0 wt. percent of the mass of the alcohol added. In some embodiments, the process can include adding CO in an amount equal to at least 0.1 wt. %, 1.0 wt. %, 2 wt. %, 3 wt. %, 4 wt. %, 5 wt. %, 6 wt. %, 7 wt. %, 8 wt. %, 9 wt. %, 10 wt. %, 15 wt. %, 20 wt. %, 25 wt. %, 30 wt. %, 40 wt. %, or 50 wt. % of the mass of the alcohol added. In some embodiments, an amount of CO can be added to achieve maximum CO solubility in water at the temperatures and pressures suitable for use in the reactions described herein.

In some embodiments, the process can include mixing one or more acids into the reaction mixture in an amount equal to at least 0.1 weight percent (wt. percent or wt. %) of the mass of the alcohol added. In some embodiments, the process can include adding one or more acids present in an amount equal to at least 1.0 wt. percent of the mass of the alcohol added. In some embodiments, the process can include adding one or more acids present in an amount equal to at least 0.1 wt. %, 1.0 wt. %, 2 wt. %, 3 wt. %, 4 wt. %, 5 wt. %, 6 wt. %, 7 wt. %, 8 wt. %, 9 wt. %, 10 wt. %, 15 wt. %, 20 wt. %, 25 wt. %, 30 wt. %, 40 wt. %, or 50 wt. % of the mass of the alcohol added.

In some embodiments, the amount of alkyl esters produced by adding $CO_2$, CO, or one or more acids can be at least 10% by weight greater than that produced by an otherwise identical reaction mixture lacking the $CO_2$, CO, and one or more acids under the same reaction conditions and residence time.

In some embodiments, the reaction mixture can include one or more organic bases or inorganic bases to further catalyze the transesterification of triglycerides to completion. In some embodiments, the reaction mixture can include a Lewis base. Some examples for suitable Lewis bases can include anions formed from the dissociation of acids such as hydrobromic acid, hydrochloric acid, hydroiodic acid, nitric acid, sulfuric acid, perchloric acid, boric acid, chloric acid, phosphoric acid, pyrophosphoric acid, chromic acid, permanganic acid, phytic acid and ethylenediamine tetramethyl phosphonic acid (EDTPA), and the like. Other Lewis bases can include, but not be limited hydroxide ion as formed from the dissociation of bases such as sodium hydroxide, potassium hydroxide, lithium hydroxide and the like. Suitable inorganic bases can include, but not be limited to lithium hydroxide, sodium hydroxide, potassium hydroxide, calcium hydroxide, strontium hydroxide, and barium hydroxide, and the like.

In some embodiments, the reaction mixture can also include a carrier compound. A carrier compound can serve various purposes including helping to reduce the viscosity of the reaction mixture. The carrier compound can be a compound that is non-reactive under the reaction conditions. Examples of carrier compounds can include, but are not limited to, hexane, saturated cycloalkanes, and fluorinated hydrocarbons. Carrier compounds can be present in the reaction mixture in an amount from 0.0 wt. % to 99.9 wt. %. Conversely, active components, such as the lipid feed stock and the alcohol feed stock can be present in the reaction mixture in an amount from 0.1 wt. % to 100.0 wt. %.

After mixing all components together to form a reaction mixture, the reaction mixture can be contacted with a catalyst at 112. In some embodiments, the catalyst can be a metal oxide catalyst. Suitable metal oxide catalysts for use herein are described more fully below. In some embodiments, step of contacting the reaction mixture with a metal catalyst can include contacting the reaction mixture with a catalyst under supercritical conditions for the alcohol. In some embodiments, step of contacting the reaction mixture with a metal catalyst can include contacting the reaction mixture with a catalyst under supercritical conditions for $CO_2$.

In some embodiments, the metal oxide catalyst can have an acid or base adsorbed thereto. In some embodiments, the metal oxide can be unmodified and does not have an acid or base adsorbed thereto. In some embodiments, the metal oxide catalyst can be disposed within a reactor having a housing. By way of example, the metal oxide catalyst can be disposed within a column. The metal oxide catalyst can be packed within the housing such that the reaction mixture must pass between particles of the metal oxide catalyst as it passes through the housing. The housing can be constructed to withstand the high pressures and temperatures associated with supercritical conditions of water, alcohols, $CO_2$, and CO. Supercritical conditions suitable for use herein are discussed further below.

After the reaction mixture is passed over the metal oxide catalyst and the reaction is driven to a desired degree of completion, the reaction products in the effluent from the reaction can be separated from one another at 114. In some embodiments, the main fraction is an alkyl ester fraction, which can be stored in a storage tank or it can be immediately utilized as biodiesel in a diesel engine. Additional byproducts of the reaction can be further separated from the rest of the reaction products. By way of example, in some embodiments, the reaction produces glycerol as a byproduct. It will be appreciated that as used herein the terms "glycerol", "glycerine" and "glycerin" are all equivalent. The glycerol can be readily separated from the alkyl esters, since glycerol has a tendency to phase separate from alkyl esters making the separation process relatively straightforward. Various types of separation devices can be used, such as a centrifugal fluid separator or the like. Additional reaction products can include aldehydes and ethers, such as dimethyl ether. The glycerol and other reaction products can be stored and later sold, used as a feed stock for other chemical processes, used as a feedstuff for animals, or used for human foods after further purification.

In some embodiments, the method may optionally include a step of removing free fatty acids from the reaction mixture, if present, at 116. This step of removing free fatty acids can also be referred to as a "polishing" step. This can be performed at various points in the production process such as before or after the step of separating reaction product at 114 and/or before or after passing the reaction mixture over the catalyst at 112.

In some embodiments, removing residual free fatty acids from the reaction mixture can include adding a compound to the reaction mixture that serves to react with the residual free fatty acids. Such as compound can be referred to as a residual free fatty acid scavenger or scavenging compound. An exemplary scavenging compound for this purpose is dimethyl carbonate. However, other compounds can also be used as a scavenging compound. In some embodiments, the scavenging compound can be added to the reaction mixture before contacting the reaction mixture with the catalyst. In other embodiments, the scavenging compound can be added after the transesterification reaction has taken place.

In some other embodiments, the residual free fatty acids in the reaction mixture can be removed in other ways. For example, a material can be used to absorb residual free fatty acids compounds. Specifically, metal oxide media containing acid/base surface properties such as Lewis acid sites, Bronsted base sites, and/or Bronsted acid sites can be used to selectively bind, at relatively low temperatures, and remove organic acids from fatty acid alkyl ester reaction products. This can be performed in various ways. In an embodiment, an appropriate metal oxide media can be disposed within the interior volume of a housing. A crude reaction product mixture containing free fatty acids can then be pumped into the housing. After contacting the metal oxide media, free fatty acids in the crude reaction product mixture can be bound to the metal oxide media. Next, the purified reaction product mixture can be separated out, leaving behind the metal oxide media and bound organic acids.

In some embodiments, the reaction can be performed under conditions sufficient to result in the production of aldehydes and/or ethers as a decomposition byproduct of glycerol instead of glycerol itself. In some embodiments, the reaction products include gases, such as dimethyl ether. While not intending to be bound by theory, the production of gases as a byproduct can be advantageous because it is believed to be easier to separate various gases from fatty acid alkyl esters than it is to separate out glycerol from fatty acid alkyl esters.

Depending on the specific metal oxide used to catalyze the reaction of lipids to form alkyl esters, a need may arise to periodically reprocess the catalyst. For example, in the context of modified metal oxide catalysts, the catalyst can be periodically retreated with an acid (such as sulfuric acid or phosphoric acid) or a base (such as sodium hydroxide). In the context of a continuous flow production facility, stopping production to reprocess the catalyst or to replace the catalyst may be costly and inefficient. As such, in some embodiments, at least two different reactors can be included such that feed stock flow can be diverted back and forth between the reactors so that one can be taken "off-line" and recharged without interrupting the production process. After the particular reactor is recharged, such as through treatment with an acid or a base, it can be returned to service.

Because the reaction mixture is passed over a metal oxide catalyst at an elevated temperature, there is a need to dissipate heat after the reaction has gone to completion. In an embodiment, heat from the effluent products is used to heat up the lipid feed stock, alcohol feed stock, $CO_2$, CO, and/or acid through a counter-flow heat exchanger. Transferring heat from the effluent flow to the feed stock flow can make the alkyl ester production process more energy efficient since less energy is used to get the reaction mixture up to the desired temperature and promotes the mixing of the reactants for faster conversion within the continuous reactor. In some embodiments the reactor housing can be a ceramic that can withstand elevated temperatures and pressures. In some embodiments, the housing reactor housing can be a metal or an alloy of metals such as INCONEL.

In some embodiments, the reaction mixture reaches the desired level of reaction completion after one pass over the metal oxide catalyst bed or packing. However, in some embodiments, the effluent flow may be rerouted over the same metal oxide catalyst or routed over another metal oxide catalyst bed or packing so that reaction is pushed farther toward completion in measured stages.

In some embodiments two or more reactors having metal oxide catalyst beds disposed therein can be used to convert lipid feed stocks to alkyl esters. For example, in some embodiments, a reaction mixture can be passed through both an acid-modified metal oxide catalyst bed and a base-modified metal oxide catalyst bed in succession. The reaction temperatures within each catalyst bed can be either the same or different. In a particular embodiment, a reaction mixture is first passed through an acid-modified metal oxide catalyst bed at a relatively lower temperature and then passed through a base-modified metal oxide catalyst bed at a relatively higher temperature. The acid-modified catalyst reaction step can serve to reduce the amount of free fatty acids in the reaction mixture before it is passed on to the base-modified catalyst reaction step.

In some embodiments, an acid-modified metal oxide catalyst (such as sulfuric or phosphoric acid modified) and a base-modified metal oxide catalyst (such as sodium hydroxide modified) can be separately formed but then disposed together within a housing. In such an approach, the reaction mixture passing through the housing can be simultaneously exposed to both the acid and base modified metal oxide catalysts.

In some embodiments, two different metal oxides (such zirconia and titania) can be separately formed but then disposed together within a reactor housing. In such an approach, the reaction mixture passing through the housing can be simultaneously exposed to both metal oxide catalysts.

It will be appreciated that the process 100 shown in FIG. 1 can be conducted in a continuous flow mode. By way of example, the process 100 can be carried out such that all of the steps are taking place simultaneously and the feedstocks, $CO_2$, CO, and/or one or more acids are continuously being resupplied and turned into biodiesel fuel. While not intending to be bound by theory, continuous flow production of biodiesel fuel can offer substantial advantages over batch production, including being more economical. However, in another embodiment, the flow may be periodically stopped to allow for the reaction to proceed to completion and then turned back on to continue the production cycle. This process of stopping and restarting flow can be referred to as a semi-continuous flow mode.

Figure 2:
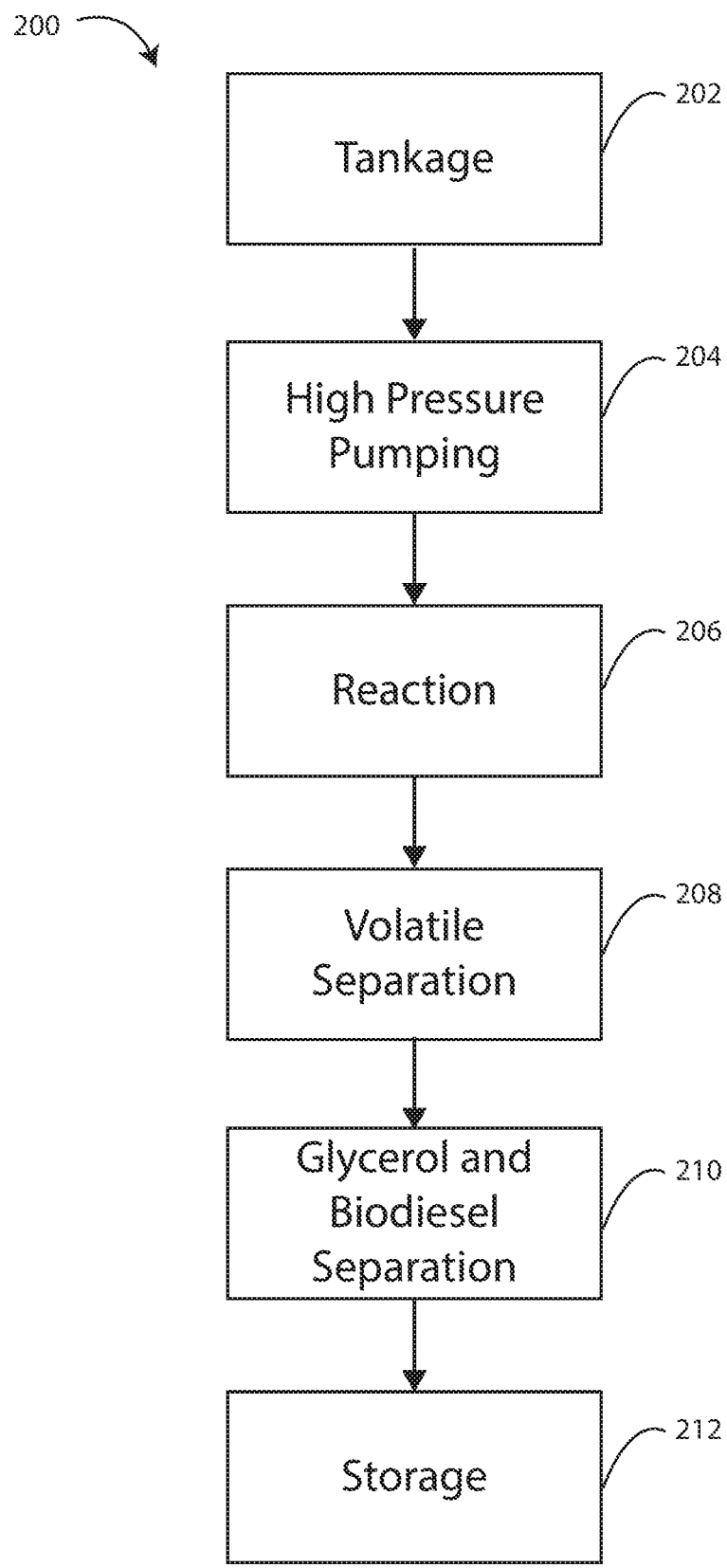
FIG. 2 is a schematic view of an exemplary process in accordance with the embodiments herein.

Referring now to FIG. 2, a schematic view is shown of a method 200 of producing alkyl esters in accordance the various embodiments herein. Reactant materials (such one or more lipid feed stocks, one or more alcohol feed stocks, $CO_2$, CO, and/or one or more acids) can be stored in tanks before being used at 202. In some embodiments each reactant can be stored in individual tanks. In other embodiments, the reactants can be mixed within the same tank. The tanks can be heated or unheated. The reactant materials can be pumped at a high pressure at 204. The high pressure can be sufficient to prevent vaporization of the feed stock materials and acids at the temperature of the reaction. Next, the feed stock materials and acids can be reacted in order to produce a reaction product composition that can include alkyl esters (such as biodiesel fuel) and byproducts (including aldehydes, ethers, and glycerol) at 206. After the reaction goes to completion, any volatile materials (such as left over alcohol or other organic compounds) and byproduct gases (such as ethers) are removed from the reaction product composition at 208. Any remaining byproducts (such as glycerol) can be separated from the alkyl esters (such as biodiesel fuel) at 210. Finally, end products such as alkyl esters and byproducts such as glycerol can be stored until being used in other processes or until being shipped away from the production plant at 212.

Figure 3:
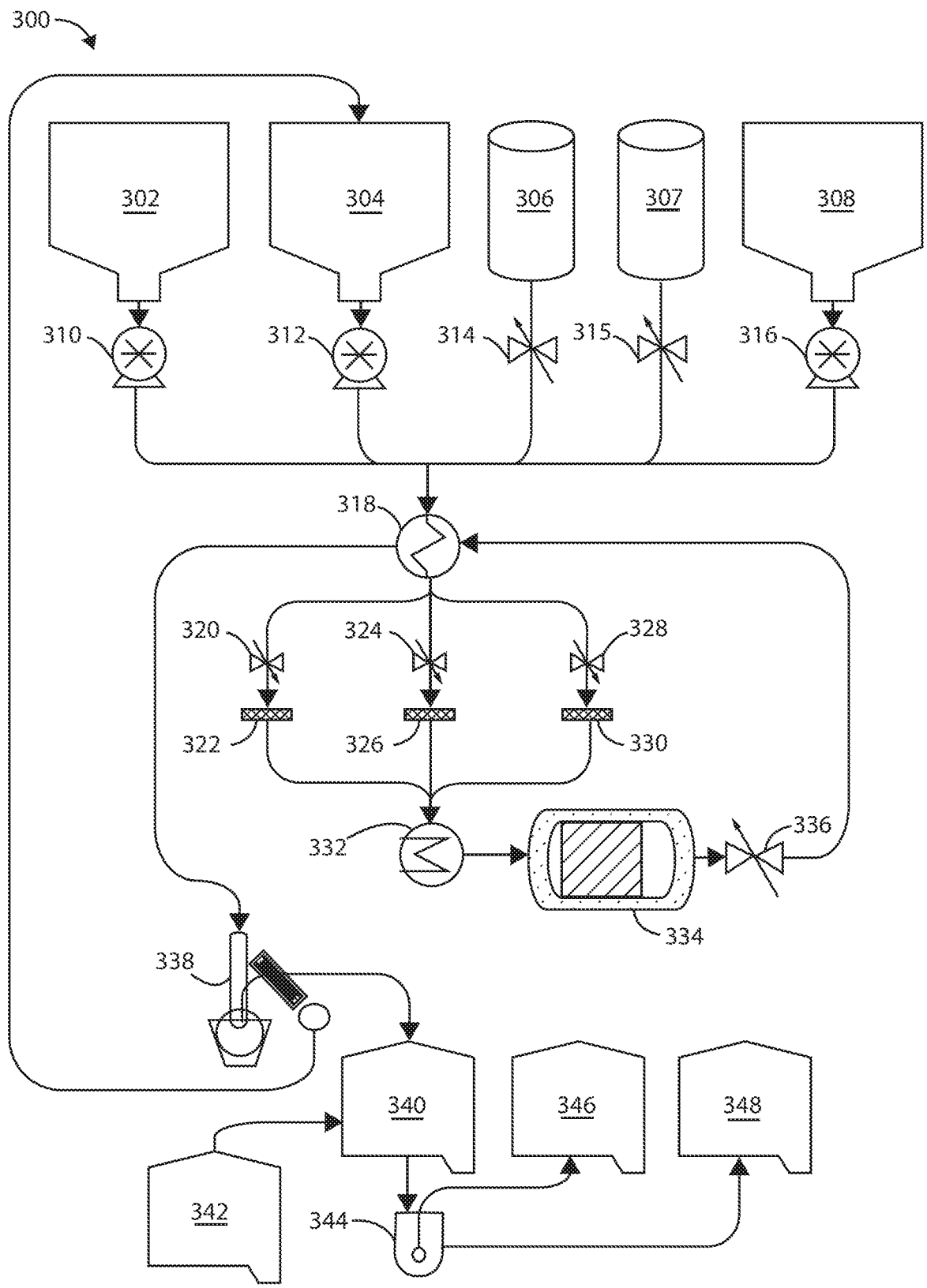
FIG. 3 is a schematic diagram of a production apparatus in accordance with the embodiments herein.

Referring now to FIG. 3, a schematic diagram is shown of an alkyl ester production apparatus 300 for producing alkyl esters in accordance with the embodiments herein. A lipid feed stock can be held in a lipid feed stock tank 302. In some embodiments, the lipid feed stock tank 302 can be heated. In some embodiments, the lipid feed stock tank 302 maintains the lipid feed stock at a temperature high enough to keep the lipid feed stock in a liquid state prior to forming a reaction mixture with other reactants. Upon exit from lipid feed stock tank 302, the lipid feed stock can pass through a lipid pump 310 before passing through a heat exchanger 318 where it can absorb heat from downstream products.

An alcohol feed stock can be held in an alcohol tank 304. Upon exit from alcohol tank 304, the alcohol feed stock can pass through an alcohol pump 312 before passing through a heat exchanger 318 where it can absorb heat from downstream products or from a pre-heater (not shown). The $CO_2$ can be held in a pressurized tank 306 and the CO can be held in a pressurized tank 307. The $CO_2$ can pass through a back pressure regulator 314 before passing through a heat exchanger 318 where it can absorb heat from downstream products from a pre-heater (not shown). The CO can pass through a back pressure regulator 315 before passing through a heat exchanger 318 where it can absorb heat from downstream products from a pre-heater (not shown).

One or more acids can be held in acid tank 308. The acid can pass through an acid pump 316 before passing through a heat exchanger 318 where it can absorb heat from downstream products from a pre-heater (not shown). In some embodiments, the heat exchanger 318 is a counter-flow heat exchanger.

An exemplary counter-flow heat exchanger is described in U.S. Pat. No. 6,666,074, the contents of which are herein incorporated by reference. For example, a pipe or tube containing the effluent flow can be routed past a pipe or tube holding the feed stock flow or the reaction mixture. In some embodiments, a pipe-in-pipe counter-flow heat exchanger can be used. In some embodiments, a thermally conductive material, such as a metal, connects the effluent flow with the feed stock flow so that heat can be efficiently transferred from the effluent products to the feed stocks or the reaction mixture.

While FIG. 3 shows $CO_2$ added as a separate reactant in parallel with other reactant materials, it will be appreciated that $CO_2$ can alternatively be mixed directly into one or more reaction tanks, including lipid feed stock tank 302, alcohol tank 304, or acid tank 308. For example, in some embodiments, the $CO_2$ can be added directly to alcohol tank 304. In other embodiments, the $CO_2$ can be added directly to a reaction mixture in the reactor 334. Similarly, while FIG. 3 shows CO added as a separate reactant in parallel with other reactant materials, it will be appreciated that CO can alternatively be mixed directly into one or more reaction tanks, including lipid feed stock tank 302, alcohol tank 304, or acid tank 308. For example, in some embodiments, the CO can be added directly to alcohol tank 304. In other embodiments, the CO can be added directly to a reaction mixture in the reactor 334.

It will be appreciated that the feed stock tanks described herein can optionally include an agitation mechanism and temperature control mechanism to keep the components in the tanks thoroughly mixed and at a relatively constant temperature. In some embodiments, one or all of the lipid, alcohol, or acid feed stock tanks may include a gas sparger/bubbler so as to displace dissolved oxygen to avoid any oxidation reactions that can potentially occur at high temperatures. In some embodiments, the tank(s) can be continuously sparged with an inert gas, such as nitrogen, to remove dissolved oxygen from the feed stocks. In some embodiments, sparging the tank(s) with nitrogen gas can further limit potential oxidation reactions. Although the lipid feed stock, the alcohol feed stock, the $CO_2$, and/or the acid feed stock in the embodiment shown in FIG. 3 are in different tanks, it will be appreciated that in some embodiments they can be disposed in the same tank.

In some embodiments the feed stocks, such as the lipid feed stock, can be processed in order to remove particulate matter and other debris before being processed through the reactor 334. By way of example, the feed stocks can be filtered or distilled. In some embodiments the feed stocks can be processed with a continuous centrifuge that can spin out all particulates and in some cases even water from the lipid feed stock.

After passing through the heat exchanger 318, the lipid feed stock passes through a shutoff valve 320 and a filter 322 to remove particulate material of a certain size from the feed stock. Similarly, the alcohol feed stock passes through a shutoff valve 324 and a filter 326, and the acid feed stock passes through shutoff valve 328 and filter 330. The lipid feed stock, alcohol feed stock, $CO_2$, CO, and/or acid feed stock then pass through a preheater 332 where they are mixed together to form a reaction mixture. The preheater 332 can elevate the temperature of the reaction mixture to a desired level. Many different types of heaters are known in the art and can be used.

It will be appreciated that while lipid feed stock, alcohol feed stock, $CO_2$, CO, and/or acid feed stock are shown in FIG. 3 as passing through separate shutoff valves and filters, they can also mix within the heat exchanger 318 and exit such that the reaction mixture containing lipid feed stock, alcohol feed stock, and $CO_2$, CO, and/or acid feed stock can pass through a single shutoff valve and filter sequence (not shown).

In some embodiments, a pre-heating step can be performed to raise the temperature of the reactants before they enter a reactor housing containing the metal oxide catalyst. Preheating of the reactants can be performed in various ways including using a heating block, a heating bath, a countercurrent heat exchanger, etc. While not intending to be bound by theory, it is believed that pre-heating the reactants can improve the efficiency of the reaction in part because of the effect pre-heating has on the maintenance of temperatures within the reactor housing. In some embodiments, the reactants can be preheated to at least about 70% of the reaction temperature inside of the reactor housing containing the metal oxide catalyst. In some embodiments, the reactants can be preheated to at least about 80% of the reaction temperature inside of the reactor housing containing the metal oxide catalyst. In some embodiments, the reactants can be preheated to at least about 90% of the reaction temperature inside of the reactor housing containing the metal oxide catalyst. In some embodiments, the reactants can be preheated to at least about 95% of the reaction temperature inside of the reactor housing containing the metal oxide catalyst. In some embodiments, the reactants can be preheated to substantially the same temperature as the reaction temperature inside of the reactor housing containing the metal oxide catalyst. In some embodiments, the reactants can be preheated to a temperature higher than the reaction temperature inside of the reactor housing containing the metal oxide catalyst. In some cases, the reactants are raised to supercritical conditions for temperature and pressure for the alcohol feed stock before entering the inside of the reactor housing. In some cases, the reactants are raised to supercritical conditions for temperature and pressure for the $CO_2$ or one or more acids before entering the inside of the reactor housing.

After preheating, the reaction mixture can then pass through a reactor 334 where the reaction mixture is converted into alkyl esters forming a reaction product mixture. The reactor 334 can include a metal oxide catalyst. For example, the reactor can include an acid (such as sulfuric acid or phosphoric acid) modified or base (such as sodium hydroxide) modified metal oxide catalyst, or an unmodified metal oxide catalyst. The reaction product mixture can pass through a backpressure regulator 336 and the heat exchanger 318 before passing on to a distillation apparatus 338. The distillation apparatus 338 can be configured to carry out fractional distillation in order to remove excess alcohol from the reaction product mixture and/or isolate one or more fractions of the biodiesel fuel that meets ASTM specifications. The distillation apparatus 338 can include any desired number of theoretical plates in order to recover a desired amount of the excess alcohol and to remove any other byproducts of the reaction. In some embodiments, the recovered alcohol can be de-watered by using molecular sieves. In some embodiments, the alcohol recovered from distillation can be put back into the alcohol tank 304 for reuse.

In many embodiments, the reaction mixture is maintained at an elevated temperature within the reactor. The reactor can be configured to withstand the temperature and pressure under which the reaction mixture is kept. In some embodiments, a heating element is in thermal communication with the reactor so as to be able to heat the reaction mixture up to the desired temperature. If the temperature of the reaction mixture is not sufficiently high, the reaction may proceed more slowly than desired. In some embodiments, the temperature of the reaction mixture is maintained at a temperature of between 200° and 400° Celsius. In some embodiments, the temperature of the reaction mixture is maintained at a temperature of between 100° and 600° Celsius. In some embodiments, the temperature of the reaction mixture is maintained at a temperature of between 350° and 400° Celsius.

In some embodiments, the temperature of the reaction mixture is about 50°, 75°, 100°, 125°, 150°, 175°, 200°, 225°, 250°, 275°, 300°, 325°, 350°, 375°, 400°, 425°, 450° 475°, 500°, 525°, 550°, 575°, 600°, 625°, 650°, 675° Celsius or hotter. It will be appreciated that temperature of the reaction mixture can fall within a range, wherein any of the forgoing temperatures can serve as the lower or upper bound of the range, provided that the lower bound of the range is a value less than the upper bound of the range. In some embodiments, the temperature of the reaction mixture can be greater than the critical temperature of the alcohol feed stock. In some embodiments, the temperature of the reaction mixture can be greater than the critical temperature of the $CO_2$ or one or more acids.

Supercritical conditions for water can include a temperature (T) of ≥350° Celsius and pressure (P) of ≥3200 psi. Supercritical conditions for the alcohols described herein can include supercritical conditions for methanol (T≥240° Celsius and P≥1150 psi) and supercritical conditions for ethanol (T≥240° Celsius and P≥890 psi). Supercritical conditions for $CO^2$ can include a T≥30° Celsius and P≥105 psi. Supercritical conditions for CO can include a T≥−140° Celsius and P≥507 psi.

However, in some embodiments, the temperature of the reaction mixture can be less than about 500° Celsius. In some embodiments, the temperature of the reaction mixture can be less than about 400° Celsius.

In some embodiments, the reaction mixture is kept under pressure. The reactor can be configured to withstand the pressure under which the reaction mixture is kept. A desirable pressure for the reaction mixture can be estimated with the aid of the Clausius-Clapeyron equation. Specifically, the Clausius-Clapeyron equation can be used to estimate the vapor pressures of a liquid. The Clausius-Clapeyron equation is as follows:

$$\ln\left(\frac{P_1}{P_2}\right) = \frac{\Delta H_{vap}}{R}\left(\frac{1}{T_2} - \frac{1}{T_1}\right)$$

wherein $\Delta H_{vap}$=is the enthalpy of vaporization; $P_1$ is the vapor pressure of a liquid at temperature $T_1$; $P_2$ is the vapor pressure of a liquid at temperature $T_2$, and R is the ideal gas law constant.

In some embodiments, the pressure inside the reactor can be greater than the vapor pressures of any of the components of the reaction mixture. In some embodiments, the pressure inside the reactor can be greater than about 500 psi, 600 psi, 700 psi, 800 psi, 900 psi, 1000 psi, 1250 psi, 1500 psi, 1750 psi, 2000 psi, 2250 psi, 2500 psi, 2750 psi, 3000 psi, 3250 psi, 3500 psi, 3750 psi, 4000 psi, 4250 psi, 4500 psi, 4750 psi, 5000 psi, 5250 psi, 5500 psi, 5750 psi, 6000 psi, 6250 psi, 6500 psi, 6750 psi, 7000 psi or higher. In some embodiments, the pressure is between about 1000 psi and about 5000 psi. In some embodiments, the pressure is between about 1500 psi and about 3500 psi. In some embodiments, the pressure is between about 500 psi and about 2000 psi. In some embodiments, the pressure inside the reactor is greater than the critical pressure of the alcohol used in the reaction. In some embodiments, the pressure inside the reactor is greater than the critical pressure of $CO_2$ or one or more acids used in the reaction.

The reaction mixture may be passed over the metal oxide catalyst within the reactor for a length of time sufficient for the reaction to reach a desired level of completion. This will in turn depend on various factors including the temperature of the reaction, the chemical nature of the catalyst, the surface area of the catalyst, and the like. The term "residence time" can be used to describe the amount of time in which the reaction product mixture interacts with the catalyst in the reactor. Embodiments herein can include methods and systems wherein the residence time is relatively small while still achieving high percentages of conversion. By way of example, in some embodiments the residence time is less than about 60 seconds. In some embodiment, the residence time is less than about 30 seconds. In some embodiment, the residence time is less than about 10 seconds.

The remaining reaction products can then pass on to a stirred tank 340 where, in some embodiments, the remaining reaction products are mixed with a base solution, such as a sodium hydroxide solution, from a base solution tank 342. The base solution can react with remaining free fatty acids in order to convert them (saponification) into a soap composition. However, it will be appreciated that in other embodiments the residual free fatty acids are removed using other methods such as those described with respect to FIG. 1 above.

The remaining reaction products and the soap composition can then pass on to a separation apparatus 344 that is configured to separate byproducts such as glycerol and the soap composition from the alkyl esters (such as biodiesel). The alkyl esters can be passed into an alkyl ester storage tank 346. The soap composition and the glycerol are can be passed into a byproduct tank 348.

In some embodiments (not shown), a metal oxide can be used as a scrubber to reduce or eliminate certain components from a reaction mixture or feed stock. By way of example, in some embodiments, unmodified zirconia, titania, and/or hafnia can be used to remove free fatty acids from compositions before or after the reaction that produces fatty acid methyl esters. As discussed above, it is believed that free fatty acids can be adsorbed to such metal oxides and therefore removed from the reaction mixture or reaction products.

One advantage of biodiesel fuel is that it can be used to operate existing diesel engines. The proper performance of diesel engines depends on a degree of consistency in the diesel fuel itself. However, various factors can affect the consistency of the fuel made by transesterification including the specific feed stocks used, the particular separation steps used, and the type of catalysis used. For these reasons, the American Society for Testing and Materials (ASTM) has created a standard for biodiesel fuel (ASTM D6751-06a). Embodiments herein can be used to produce a mixture of alkyl esters that meets the specifications of ASTM D6751-06a. Specifically, embodiments herein can include alkyl ester solutions complying with ASTM D6751-06a.

Embodiments can also include a diesel fuel composition including fatty acid alkyl esters as the reaction product of a biological lipid feed stock including triglycerides, an alcohol feedstock, $CO_2$, CO, and/or an acid, wherein at least about 50%, 60%, 70%, 75%, 80%, 85%, 90%, 95%, 97%, 98%, or 99% of the triglycerides on a molar basis are converted into fatty acid methyl esters.

Lipid Feed Stocks

Lipid feed stocks suitable for use with the embodiments herein can be derived from many different sources. In some embodiments, lipid feed stocks can include biological lipid feed stocks. Biological lipid feed stocks can include lipids (e.g., fats or oils) produced by any type of microorganism, plant, or animal. In an embodiment, the biological lipid feed stocks used can include triglycerides. Many different biological lipid feed stocks derived from plants can be used. By way of example, plant-based lipid feed stocks can include rapeseed oil, soybean oil (including degummed soybean oil), canola oil, cottonseed oil, grape seed oil, mustard seed oil, corn oil, linseed oil, safflower oil, sunflower oil, poppy-seed oil, pecan oil, walnut oil, oat oil, peanut oil, rice bran oil, *Camellia* oil, castor oil, and olive oil, palm oil, coconut oil, rice oil, algae oil, seaweed oil, Chinese Tallow tree oil. Other plant-based biological lipid feed stocks can be obtained from argan, avocado, babassu palm, balanites, borneo tallow nut, brazil nut, *Calendula*, camelina, caryocar, cashew nut, chinese vegetable tallow, cocoa, coffee, cohune palm, coriander, cucurbitaceae, *Euphorbia*, hemp, illipe, jatropha, jojoba, kenaf, kusum, macadamia nuts, mango seed, noog *Abyssinia*, nutmeg, opium poppy, *Perilla*, pili nut, pumpkin seed, rice bran, sacha inche, seje, sesame, shea nut, teased, allanblackia, almond, chaulmoogra, *Cuphea, Jatropa* curgas, karanj a seed, neem, *Papaya*, tonka bean, tung, and ucuuba, cajuput, *Clausena anisata*, davana, *galbanum* natural oleoresin, german chamomile, hexastylis, high-geraniol monarda, juniapa-hinojo sabalero, lupine, *Melissa officinalis*, milfoil, ninde, patchouli, tarragon, and wormwood.

Many different lipid feed stocks derived from animals can also be used. By way of example, animal-based biological lipid feed stocks can include, but not be limited to, choice white grease, lard (pork fat), tallow (beef fat), fish oil, and poultry fat.

Many different lipid feed stocks derived from microorganisms (e.g., Eukaryotes, Eubacteria and Archaea) can also be used. By way of example, microbe-based lipid feed stocks can include, but not be limited to, the L-glycerol lipids of Archaea and algae and diatom oils.

In some embodiments, lipid feed stocks derived from both plant and animal sources can be used such as yellow grease, white grease, and brown grease. By way of example, yellow, white or brown grease can include, but not be limited to, frying oils from deep fryers and can thus include fats of both plant and animal origin. Lipid feed stocks can specifically include used cooking oil. Brown grease (also known as trap grease) can include fats extracted from sewage systems and can thus include fats of both plant and animal origin. In some embodiments, lipid feed stocks used in embodiments herein can include non-biological lipid feed stocks. Lipid feed stocks suitable for use herein can include black oil.

In some embodiments, lipid feed stocks can be derived from microorganisms such as bacteria, protozoa, algae, and fungi. Lipid feed stocks suitable for use herein can also include soap stock and acidulated soap stock.

Lipid feed stocks suitable for use with the embodiments herein can specifically include low value feed stocks. Low value feed stocks, such as various types of animals fats and waste oils, generally have a relatively high concentration of free fatty acids. One method of assessing the concentration of free fatty acids is to determine the acid number (or acid value) of the feed stock. The acid number is the mass of potassium hydroxide (KOH) in milligrams that is required to neutralize one gram of the chemical substance being assessed. The precise acid number as measured can vary because of the heterogeneity of the lipid feed stock. However, as an example, a high value feed stock such as virgin soybean oil can have an acid number of about 0.35 whereas a lower value feed stock such as swine tallow can have an acid number of about 5. Yellow grease, a low value feed stock, can have an acid number of about 15 while acidulated soap stock, also a low value feed stock, can have an acid number of about 88.

Systems and methods herein can advantageously use low value feed stocks in order to produce biodiesel fuel while achieving high percent conversion rates. In some embodiments, the lipid feed stock used has an acid number of about 3 (mg KOH/g oil) or greater. In some embodiments, the lipid feed stock used has an acid number of about 5 (mg KOH/g oil) or greater. In some embodiments, the lipid feed stock used has an acid number of about 10 (mg KOH/g oil) or greater. In some embodiments, the lipid feed stock used has an acid number of about 50 (mg KOH/g oil) or greater. In some embodiments, the lipid feed stock can be converted from one having an acid number of greater than or equal to 3 (mg KOH/g oil) to an acid number of less than or equal to 0.5 (mg KOH/g oil). In some embodiments, the lipid feed stock can be converted from one having an acid number of greater than or equal to 3 (mg KOH/g oil) to an acid number of essentially 0 (mg KOH/g oil).

Alcohols

Alcohols suitable for use with the embodiments herein can include many different types of alcohols. By way of example, the alcohols can include those having from one to six carbon atoms. For example, in some embodiments, methanol is used. Methanol can be advantageous as the resulting alkyl esters (methyl esters) have a lower viscosity than higher alkyl esters. However, in some embodiments ethanol is used. Ethanol has low toxicity and is readily produced from plant matter by fermentation processes. In some embodiments, the alcohols used herein are around 95% to 97% pure, with the balance being made up of water. Without wishing to be bound by theory, it is believed that adding $CO_2$ to the alcohol feed stock or to the reaction mixture can result in the formation of carbonic acid within the water fraction of the alcohol feedstock or the reaction mixture. It is further believed that having carbonic acid and/or one or more acids present in the reaction mixture can increase the rate of esterification and/or transesterification and drive the reaction to completion such that the acid number is less than 0.5. In some embodiments, the reaction can be driven to completion such that the acid number is close to zero.

In some embodiments, the alcohols used herein can include water present in an amount equal to at least 0.05 wt. %, 0.1 wt. %, 1.0 wt. %, 2 wt. %, 3 wt. %, 4 wt. %, 5 wt. %, 6 wt. %, 7 wt. %, 8 wt. %, 9 wt. %, 10 wt. %, 15 wt. %, 20 wt. %, 25 wt. %, 30 wt. %, 40 wt. %, or 50 wt. % of the mass of the alcohol solution added. It will be appreciated that amount of water present in the alcohols suitable for use herein can be within a range, wherein any of the forgoing weight percentages can serve as the lower or upper bound of the range, provided that the lower bound of the range is a value less than the upper bound of the range.

In some embodiments, a single alcohol is used. In other embodiments, a mixture of different alcohols is used. By way of example, a mixture of methanol and a higher molecular weight alcohol can be used. Such a mixture can offer the advantage of being more miscible with the biological lipid feed stock than methanol alone.

Acids

Acids suitable for use with the embodiments herein can include many different types of acids. Without being bound by theory, it is believed that addition of acid can further catalyze the esterification of free fatty acids present in feed stocks or those that arise from the lipolysis of triglycerides during processing. By way of example, the acids can include one or more of an organic acid, an inorganic acid, a Bronsted acid, or a Lewis acid. Suitable organic acids for use herein can include, but not be limited to formic, acetic, propionic, butyric, valeric, caproic, oxalic, lactic, malic, citric, benzoic, carbonic, phenol, and uric acids, and the like. Suitable inorganic acids for use herein can include, but not be limited to, hydrochloric, nitric, phosphoric, sulfuric, boric, chloric, hydrofluoric, hydrobromic, perchloric, and hydroiodic acids. It will be appreciated that suitable Bronsted acids can include any of the forgoing organic acids or inorganic acids. Additional Bronsted acids can be include pyrophosphoric acid, methanethiol, chromic acid, permanganic acid, phytic acid and ethylenediamine tetramethyl phosphonic acid (EDTPA). Suitable Lewis acids can include, but not be limited to trimethylamine, tetrhydrofuran, diethylether, acetonitrile, quinuclidine, pyridine, acetone, ethylacetate, dimethylsulfoxide, dimethylacetamide, tetryhydrothiophene, trimethylphosphine, and the like.

Catalysts

Catalysts herein can include those exhibiting sufficient stability in the presence of supercritical conditions for the alcohols and acids described herein. For example, the supercritical conditions for methanol include T≥240° Celsius and P≥1150 psi and the supercritical conditions for ethanol include T≥240° Celsius and P≥890 psi. In some embodiments, the catalysts herein can include those exhibiting sufficient stability in the presence of supercritical temperatures and pressures for water (i.e., T≥350° Celsius and P≥3200 psi).

Catalysts herein can include metals, metal oxides, ceramics, and the like. Catalysts used with embodiments herein can include metal oxides with surfaces including Lewis acid sites, Bronsted base sites, and Bronsted acid sites. By definition, a Lewis acid is an electron pair acceptor. A Bronsted base is a proton acceptor and a Bronsted acid is a proton donor. In some embodiments, the metal oxide catalyst has been pretreated with a Bronsted acid or a Bronsted base. In some embodiments, the metal oxide catalyst can be treated with a Bronsted, including but not limited to, hydrobromic acid, hydrochloric acid, hydroiodic acid, nitric acid, sulfuric acid, perchloric acid, boric acid, chloric acid, phosphoric acid, pyrophosphoric acid, methanethiol, chromic acid, permanganic acid, phytic acid and ethylenediamine tetramethyl phosphonic acid (EDTPA).

Catalysts of embodiments herein can specifically include unmodified metal oxides including zirconia, titania, hafnia, yttria, tungsten (VI) oxide, manganese oxide, nickel oxide, nickel, copper oxide, niobium oxide, cobalt oxide, carbon, carbon/nickel, carbon/platinum. In some embodiments catalysts can include alumina, iron oxide, metal salts, insoluble metal salts, metal oxides, metal hydroxides, metal alloys, metal complexes, and metal ion complexes. Metals of these can include alkali metals, alkaline earth metals, transition metals and poor metals. In some embodiments, the metal can include one or more of group IA, IIA, IIB, IVB, VB, VIB, VIIB, VIIIB, IB, IIB, IIIA, IVA metals. In some embodiments, the catalyst can include one or more of $CuO$, $KH_2PO_4$, $Nb_2O_5$, $Y_2O_3$, $ZnO$, $MgCO_3$, $K_2CO_3$, $Fe_2O_3$, and $CoO_2$. In some embodiments, the catalyst can consist essentially of one or more of any of the materials described herein.

In some embodiments, the catalyst can be, or include, a metal oxide that is stable at temperatures above 250° Celsius in the presence of supercritical alcohol. In some embodiments, the catalyst can be, or include, a metal oxide that is stable at temperatures above 350° Celsius in the presence of supercritical alcohol. In some embodiments, the catalyst can be, or include, a metal oxide that is stable at temperatures above 400° Celsius in the presence of supercritical alcohol. In some embodiments, the catalyst can be, or include, a metal oxide that is stable at temperatures above 450° Celsius in the presence of supercritical alcohol. In some embodiments, the catalyst can be, or include, a metal oxide that is stable at temperatures above 500° Celsius in the presence of supercritical water. In some embodiments, the catalyst can consist essentially of any of the foregoing.

In some embodiments, the catalyst can be, or include, a metal oxide that is stable at temperatures above 350° Celsius in the presence of supercritical water. In some embodiments, the catalyst can be, or include, a metal oxide that is stable at temperatures above 400° Celsius in the presence of supercritical water. In some embodiments, the catalyst can be, or include, a metal oxide that is stable at temperatures above 450° Celsius in the presence of supercritical water. In some embodiments, the catalyst can be, or include, a metal oxide that is stable at temperatures above 500° Celsius in the presence of supercritical water. In some embodiments, the catalyst can be, or include, a metal oxide that is stable at temperatures above 550° Celsius in the presence of supercritical water. In some embodiments, the catalyst can consist essentially of any of the foregoing.

Catalysts of embodiments herein can also include silica clad with any of the foregoing catalyst materials, such as a metal oxide selected from the group consisting of zirconia, titania, hafnia, yttria, tungsten (VI) oxide, manganese oxide, nickel oxide, nickel, copper oxide, niobium oxide, cobalt oxide, carbon carbon/nickel, carbon/platinum.

In some embodiments, the catalyst can be of a single metal oxide type. By way of example, in some embodiments, the catalyst is substantially pure zirconia. By way of example, in some embodiments, the catalyst is substantially pure titania. By way of example, in some embodiments, the catalyst is substantially pure hafnia. By way of example, in some embodiments, the catalyst is substantially pure yttria. By way of example, in some embodiments, the catalyst is substantially pure tungsten (VI) oxide. By way of example, in some embodiments, the catalyst is substantially pure manganese oxide. By way of example, in some embodiments, the catalyst is substantially pure nickel oxide.

Catalysts of embodiments herein can also include mixtures of materials, such as mixtures of materials including zirconia, titania, hafnia, yttria, tungsten (VI) oxide, manganese oxide, nickel oxide, nickel, carbon, carbon/nickel, and carbon/platinum.

In some embodiments, the catalyst can consist essentially of zirconia. Zirconia catalyst particles for use herein can be thermally and chemically stable under supercritical alcohol conditions (e.g., T≥240° Celsius and P≥850 psi). Zirconia catalyst particles for use herein can also be thermally and chemically stable under supercritical water conditions (i.e., T≥350° Celsius and P≥3,200 psi). Exemplary zirconia catalysts are commercially available from ZirChrom Separations of Anoka, Minn. Suitable zirconia catalyst particles for use herein can maintain a well-defined pore structure and are stable under both high pressure (6,000 psi) and high temperature (600° Celsius) conditions. In some embodiments, the zirconia catalyst can be porous and spherical, with an average diameter of 25 microns. Zirconia is also well-suited for the embodiments herein due to its high chemical stability over the entire pH range, from pH of 1 to a pH of 14.

Metal oxide catalysts of embodiments herein can include metal oxide particles clad with carbon. Carbon clad metal oxide particles can be made using various techniques such as the procedures described in U.S. Pat. Nos. 5,108,597; 5,254,262; 5,346,619; 5,271,833; and 5,182,016, the contents of which are herein incorporated by reference. Carbon cladding on metal oxide particles can render the surface of the particles more hydrophobic.

Metal oxide catalysts suitable for use herein can also include polymer coated metal oxides. By way of example, metal oxides herein can include a metal oxide coated with polybutadiene (PBD). Polymer coated metal oxide particles can be made using various techniques such as the procedure described in Example 1 of U.S. Pub. No. 2005/0118409, the content of which is herein incorporated by reference. Polymer coatings on metal oxide particles can render the surface of the particles more hydrophobic.

Metal oxide catalysts of embodiments herein can be made in various ways. As one example, a colloidal dispersion of zirconium dioxide can be spray dried to produce aggregated zirconium dioxide particles. Colloidal dispersions of zirconium dioxide are commercially available from Nyacol Nano Technologies, Inc., Ashland, Mass. The average diameter of particles produced using a spray drying technique can be varied by changing the spray drying conditions. Examples of spray drying techniques are described in U.S. Pat. Nos. 4,138,336 and 5,108,597, the contents of both of which are herein incorporated by reference. It will be appreciated that other methods can also be used to create metal oxide particles. One example is an oil emulsion technique as described in Robichaud et al., Technical Note, "An Improved Oil Emulsion Synthesis Method for Large, Porous Zirconia Particles for Packed- or Fluidized-Bed Protein Chromatography," Sep. Sci. Technol. 32, 2547-59 (1997). A second example is the formation of metal oxide particles by polymer induced colloidal aggregation as described in M. J. Annen, R. Kizhappali, P. W. Carr, and A. McCormick, "Development of Porous Zirconia Spheres by Polymerization-Induced Colloid Aggregation-Effect of Polymerization Rate," J. Mater. Sci. 29, 6123-30 (1994). A polymer induced colloidal aggregation technique is also described in U.S. Pat. No. 5,540,834, the contents of which are herein incorporated by reference.

Metal oxide catalysts suitable for use in the embodiments herein can be sintered by heating them in a furnace or other heating device at a relatively high temperature. In some embodiments, the metal oxide is sintered at a temperature of about 160° C. or greater. In some embodiments, the metal oxide is sintered at a temperature of about 400° C. or greater. In some embodiments, the metal oxide is sintered at a temperature of about 600° C. or greater. Sintering can be done for various amounts of time depending on the desired effect. Sintering can make metal oxide catalysts more durable. In some embodiments, the metal oxide is sintered for more than about 30 minutes. In some embodiments, the metal oxide is sintered for more than about 3 hours. However, sintering also reduces the surface area. In some embodiments, the metal oxide is sintered for less than about 1 week.

In some embodiments, the catalyst is in the form of particles. Particles within a desired size range can be specifically selected for use as a catalyst. For example, particles can be sorted by size using techniques such as air classification, elutriation, settling fractionation, or mechanical screening. In some embodiments, the size of the particles is greater than about 0.2 μm. In some embodiments, the size range selected is from about 50 nm to about 50 mm. In some embodiments, the size range selected is from about 0.2 m to about 10 mm. In some embodiments, the size range selected is from about 0.2 m to about 5 mm. In some embodiments, the size range selected is from about 0.2 m to about 2 mm. In some embodiments, the size range selected is from about 0.2 m to about 1 mm. In some embodiments, the size range selected is from about 1 m to about 100 μm. In some embodiments, the size range selected is from about 5 μm to about 15 μm. In some embodiments, the average size selected is about 10 μm. In some embodiments the size of the particles is about 80 μm. In some embodiments the size of the particles is about 25-35 μm. In some embodiments, the average size selected is about 5 μm.

In some embodiments, the catalyst can be a particulate in the nanometer size range. In some embodiments, the catalyst can be from about 0.1 nm to about 500 nm. In some embodiments, the catalyst can be from about 1.0 nm to about 300 nm. In some embodiments, the catalyst can be from about 5.0 nm to about 200 nm. In some embodiments, the catalyst can be used in the form of a colloid.

In some embodiments, catalyst particles used herein are porous. By way of example, in some embodiments the particles can have an average pore size of about 30 angstroms to about 2000 angstroms. However, in other embodiments, catalyst particles used are non-porous.

The physical properties of a porous catalyst can be quantitatively described in various ways such as by surface area, pore volume, porosity, and pore diameter. In some embodiments, catalysts of embodiments herein can have a surface area of between about 1 and about 1000 $m^2$/gram. In some embodiments, catalysts of embodiments herein can have a surface area of between about 1 and about 400 $m^2$/gram. In some embodiments, the catalyst of embodiments herein can have a surface area much higher than 400 $m^2$/gram.

In some embodiments, catalysts of embodiments herein can have a surface area of between about 1 and about 200 $m^2$/gram. Pore volume refers to the proportion of the total volume taken up by pores in a material per weight amount of the material. In some embodiments, catalysts of embodiments herein can have a pore volume of between about 0.01 ml/g and about 2 ml/g. In some embodiments, catalysts of embodiments herein can have a pore volume of between about 0 ml/gram and 0.6 ml/gram. Porosity refers to the proportion within a total volume that is taken up by pores. As such, if the total volume of a particle is 1 $cm^3$ and it has a porosity of 0.5, then the volume taken up by pores within the total volume is 0.5 $cm^3$. In some embodiments, catalysts of embodiments herein can have a porosity of between about 0 and about 0.8. In some embodiments, catalysts of embodiments herein can have a porosity of between about 0.3 and 0.6.

Catalyst particles used with embodiments herein can have various shapes. By way of example, in some embodiments the particle can be in the form of spherules. In other embodiments, the particle can be a monolith. In some embodiments, the particle can have an irregular shape.

Metal oxides suitable for use with the embodiments herein can include metal oxides whose surfaces are dominated by Lewis acid-base chemistry. A Lewis acid is an electron pair acceptor. Metal oxides herein can have Lewis acid sites on their surface and can specifically include alumina, zirconia, titania and hafnia. Metal oxides herein can also include silica clad with a metal oxide selected from the group consisting of zirconia, alumina, titania, hafnia, zinc oxide, copper oxide, magnesium oxide and iron oxide. In some embodiments, metal oxides can include yttria (yttrium oxide), such as ytrria stabilized zirconia. In some embodiments, metal oxides can include magnesium oxide and/or cerium dioxide. Metal oxides herein can also include mixtures of metal oxides. Specifically metal oxides herein can include mixtures including one or more of zirconia, alumina, titania and hafnia.

One issue associated with many previous methods for producing biodiesel is that the catalysts used are subject to poisoning over time. Specifically, many existing catalysts are affected by the reaction conditions (e.g., pH, temperature, pressure) in a manner so as to reduce reaction yield over time. However, some embodiments of metal oxide catalysts as described herein are advantageous because they are highly resistant to poisoning over time. This is particularly significant in the context of supercritical reaction conditions, which may otherwise tend to promote catalyst poisoning. Of the various metal oxides that can be used with embodiments herein, zirconia, titania and hafnia offer particular advantages because they are very chemically and thermally stable and can withstand very high temperatures and pressures (such as supercritical conditions for various alcohols) as well as extremes in pH. Such catalysts can exhibit a resistance to poisoning over time. In some embodiments, the metal oxide catalyst can include zirconia, titania, and/or hafnia. Zirconia and hafnia are even more thermally stable than titania. In some embodiments, the metal oxide catalyst can include zirconia and/or hafnia.

Some feed stocks may include components, such as lecithin, that can lead to the deposit of residues resulting in clogging and/or obstruction of a transesterification reactor. The significant thermal stability of metal oxides used with embodiments herein can be advantageous in this context because the reactor can be cleaned out through the use of an oxygen containing gas or liquid at extremely high temperatures to combust any residue that has been deposited on the metal oxide catalyst, thereby cleaning the reactor and returning it to its original state. Other types of catalysts may not have sufficient thermal stability to perform such a cleaning/regeneration process.

In some embodiments, the metal oxides suitable for use with the embodiments herein can be bare or unmodified. As used herein, the term "unmodified metal oxide" shall refer to a metal oxide that includes substantially only the metal oxide at its surface, and thus does not include significant concentrations of chemical groups such as phosphates or sulfates on its surface. Many conventional catalyst materials include various modifying groups to enhance catalysis. However, as shown in the examples herein, unmodified metal oxides can surprisingly be used to achieve high conversion percentages and relatively small residence times.

However, in other embodiments, metal oxides suitable for use herein can be modified with another compound. For example, the Lewis acid sites on metal oxides can interact with Lewis basic compounds. Thus, metal oxides herein can be modified by adsorbing Lewis basic compounds to the surface of metal oxides. A Lewis base is an electron pair donor. Lewis basic compounds herein can include anions formed from the dissociation of acids such as hydrobromic acid, hydrochloric acid, hydroiodic acid, nitric acid, sulfuric acid, perchloric acid, boric acid, chloric acid, phosphoric acid, pyrophosphoric acid, methanethiol, chromic acid, permanganic acid, phytic acid and ethylenediamine tetramethyl phosphonic acid (EDTPA).

While not intending to be bound by theory, the use of strong acids as a modifying agent for the metal oxide catalysts herein can be advantageous because they absorb more strongly to the Lewis acid sites on the metal oxide and thus be less likely to leach off into the reaction mixture. Exemplary acids include phosphoric acid.

Lewis basic compounds to be used as a modifying agent for the metal oxide catalysts herein can include hydroxide ion as formed from the dissociation of bases such as sodium hydroxide, potassium hydroxide, lithium hydroxide and the like.

The Lewis acid sites on catalysts of embodiments herein can interact with Lewis basic compounds. Thus, in some embodiments, Lewis basic compounds can be bonded to the surface of catalysts. However, in other embodiments, the catalysts used with embodiments herein are unmodified and have no Lewis basic compounds bonded thereto. A Lewis base is an electron pair donor. Lewis basic compounds of embodiments herein can include anions formed from the dissociation of acids such as hydrobromic acid, hydrochloric acid, hydroiodic acid, nitric acid, sulfuric acid, perchloric acid, boric acid, chloric acid, phosphoric acid, pyrophosphoric acid, chromic acid, permanganic acid, phytic acid and ethylenediamine tetramethyl phosphonic acid (EDTPA), and the like. Lewis basic compounds of embodiments herein can also include hydroxide ion as formed from the dissociation of bases such as sodium hydroxide, potassium hydroxide, lithium hydroxide and the like.

The anion of an acid can be bonded to a metal oxide of embodiments herein by refluxing the metal oxide in an acid solution. By way of example, metal oxide particles can be refluxed in a solution of sulfuric acid. Alternatively, the anion formed from dissociation of a base, such as the hydroxide ion formed from dissociation of sodium hydroxide, can be bonded to a metal oxide by refluxing in a base solution. By way of example, metal oxide particles can be refluxed in a solution of sodium hydroxide. The base or acid modification can be achieved under exposure to the acid or base in either batch or continuous flow conditions when disposed in a reactor housing at elevated temperature and pressure to speed up the adsorption/modification process. In some embodiments, fluoride ion, such as formed by the dissociation of sodium fluoride, can be bonded to the particles.

In some embodiments, catalyst particles can be packed into a housing, such as a column. In some embodiments, the column is a reactor. The metal oxide particles disposed in a housing can form a fixed-bed reactor. Disposing catalyst particles in a housing is one approach to facilitating continuous flow processes. Many different techniques can be used for packing the catalyst particles into a housing. The specific technique used may depend on factors such as the average particle size, the type of housing used, etc. Generally speaking, particles with an average size of about 1-20 microns can be packed under pressure and particles with an average size larger than 20 microns can be packed by dry-packing/tapping methods or by low pressure slurry packing. In some embodiments, the catalyst particles of embodiments herein can be impregnated into a membrane, such as a PTFE membrane.

However, in some embodiments, catalysts used with embodiments herein are not in particulate form. For example, a layer of a metal oxide can be disposed on a substrate in order to form a catalyst. The substrate can be a surface that is configured to contact the feedstocks during processing. In one approach, a catalyst can be disposed as a layer over a surface of a reactor that contacts the feedstocks. Alternatively, the catalyst can be embedded as a particulate in the surface of an element that is configured to contact the feedstocks during processing.

Example 1: Formation of Alkyl Esters

A fixed-bed reactor reaction vessel is packed with a particulate titania catalyst. A lipid feed stock is mixed with methanol. The lipid feed stock has an acid number of less than 3 mg KOH/g oil. Carbon dioxide is added to the mixture. The mixture is pumped under pressure into the fixed-bed reactor reaction vessel. The pressure and temperature in the reaction vessel are supercritical for methanol. The pressure in the reaction vessel is greater than 1154 PSI and the temperature is greater than 240 degrees Celsius. A reaction product mixture is obtained. The reaction product mixture includes alkyl esters.

Example 2: Formation of Alkyl Esters

A fixed-bed reactor reaction vessel is packed with a particulate zirconia catalyst. A lipid feed stock is mixed with ethanol. The lipid feed stock has an acid number of greater than 3 mg KOH/g oil. Carbon dioxide is added to the mixture. The mixture is pumped under pressure into a fixed-bed reactor reaction vessel. The pressure and temperature in the reaction vessel are supercritical for ethanol. The pressure in the reaction vessel is greater than 915 PSI and the temperature is greater than 240.9 degrees Celsius. A reaction product mixture is obtained. The reaction product mixture includes alkyl esters.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A process for producing alkyl esters comprising:
   mixing a lipid feed stock with an alcohol, water and at least one of carbon dioxide and/or one or more acids to form a reaction mixture; and
   contacting the reaction mixture with a catalyst under supercritical conditions for the alcohol,
   the catalyst comprising a metal oxide; and
   wherein an amount of alkyl esters is produced that is at least 10% by weight greater than that produced by an otherwise identical reaction mixture lacking the carbon dioxide and one or more acids under the same reaction conditions and residence time.

2. The process of claim 1, the metal oxide selected from the group consisting of alumina, titania, zirconia, and hafnia.

3. The process of claim 1, the lipid feed stock having an acid number of greater than or equal to 3 mg KOH/g oil.

4. The process of claim 3, wherein the step of contacting the reaction mixture with a catalyst comprises conversion of the lipid feed stock from an acid number of equal to 3 mg KOH/g oil to an acid number of less than or equal to 0.5 mg KOH/g oil.

5. The process of claim 1, the acid comprising an organic acid.

6. The process of claim 1, the acid comprising a Bronsted acid.

7. The process of claim 1, the acid comprising an inorganic acid.

8. The process of claim 1, further including mixing an inorganic base or an organic base into the reaction mixture.

9. The process of claim 1, wherein the step of contacting the reaction mixture with a catalyst is performed at a temperature of between 200 and 400 degrees Celsius.

10. The process of claim 1, wherein the step of contacting the reaction mixture with a catalyst is performed at a pressure of between 1000 and 5000 psi.

11. The process of claim 1, wherein the catalyst has a porosity of between 0.3 and 0.6.

12. The process of claim 1, wherein carbon dioxide is present in an amount equal to at least 0.1 wt. percent of the mass of the alcohol added.

13. The process of claim 1, wherein carbon dioxide is present in an amount equal to at least 0.5 wt. percent of the mass of the alcohol added.

14. The process of claim 1, the reaction mixture comprising carbonic acid at concentration of at least 0.05 M.

15. The process of claim 1, the reaction mixture comprising carbonic acid at concentration of at least 1 M.

16. The process of claim 1, wherein the pH of the reaction mixture is less than 7.

17. The process of claim 1, wherein the pH of the reaction mixture is less than 3.

18. A process for producing alkyl esters comprising:
   mixing a lipid feed stock with an alcohol, water and at least one of carbon dioxide and/or one or more acids to form a reaction mixture; and
   contacting the reaction mixture with a catalyst under supercritical conditions for the alcohol,
   the catalyst comprising a metal oxide; and
   wherein the catalyst comprises particles with an average particle size of 0.2 microns to 2 millimeters.

19. A process for producing alkyl esters comprising:
   mixing a lipid feed stock with an alcohol, water and at least one of carbon dioxide and/or one or more acids to form a reaction mixture; and
   contacting the reaction mixture with a catalyst under supercritical conditions for the alcohol,
   the catalyst comprising a metal oxide; and
   wherein the catalyst comprises a pore volume of between 0 and 0.6 ml/gram.

* * * * *